United States Patent
Lavielle et al.

Patent Number: 5,077,288
Date of Patent: Dec. 31, 1991

[54] 4-FLUOROBENZOIC COMPOUNDS WITH 5-HT$_2$- AND $\alpha_1$-ANTAGONISTIC ACTIVITIES

[75] Inventors: Gilbert Lavielle, La Celle Saint Cloud; Francis Colpaert, Le Vesinet; Michel Laubie, Vaucresson, all of France

[73] Assignee: Adir et Compagnie, Neuilly-sur-Seine, France

[21] Appl. No.: 496,279

[22] Filed: Mar. 20, 1990

[30] Foreign Application Priority Data

Mar. 21, 1989 [FR] France ............... 89 03653

[51] Int. Cl.$^5$ ............... A61K 31/395; A61K 31/505; C07D 403/00; C07D 487/00
[52] U.S. Cl. ............... 514/210; 514/212; 514/248; 514/252; 514/253; 514/257; 514/258; 514/315; 514/321; 540/480; 540/481; 540/450; 540/484; 544/281; 544/285; 544/237; 544/259; 544/360; 544/365; 544/295; 548/950; 548/953; 548/539; 548/571; 548/526; 548/225; 548/237
[58] Field of Search ............... 544/281, 285, 237, 255, 544/259, 360, 365, 295; 540/480, 481, 450, 484, 596, 598, 599, 600, 610; 548/950, 953, 539, 571, 526, 225, 237; 514/210, 212, 248, 252, 253, 257, 258, 315, 321, 423, 428

[56] References Cited

U.S. PATENT DOCUMENTS
4,335,127  6/1982  Vandenberk et al. ............... 424/251

OTHER PUBLICATIONS
Vandenberk, J. Chem. Abstr. 94:65718a (1981).
Vandenberk, J. Chem. Abstr. 96:216,203 (1982).

Primary Examiner—Mukund J. Shah
Assistant Examiner—Matthew V. Grumbling
Attorney, Agent, or Firm—Gordon W. Hueschen

[57] ABSTRACT

The invention relates to the compounds of general formula I:

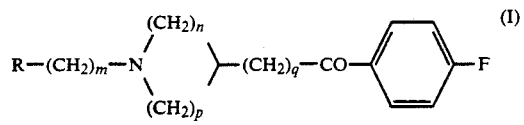

in which:
m represents an integer from 2 to 4,
n and p, which may be identical or different, each represent an integer from 1 to 3,
q represents 0 or 1, and
R represents:
either a group of formula (A):

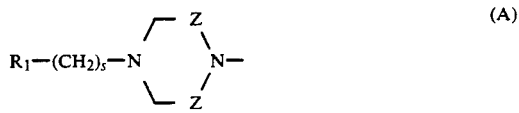

or a radical of formula (B):

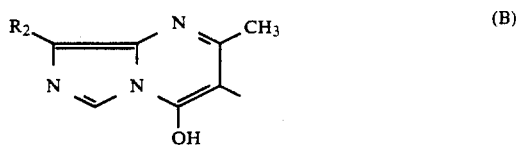

or a 2,4-dioxo-1,2,3,4-tetrahydroquinazolinyl radical, on condition, however, that, in this case, n and p do not simultaneously represent the number 2,
or a benzhydryloxy group,
or a 1-oxophthalazinyl radical,
or a 5-oxothiazolo[3,2-A]pyrimidinyl radical,
or a group of formula C:

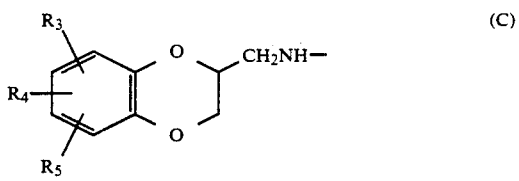

their possible stereoisomers and their addition salts with a pharmaceutically acceptable inorganic or organic acid.

The compounds of formula I are medicinal products with useful 5-HT$_2$- and $\alpha_1$-antagonistic activities.

11 Claims, No Drawings

4-FLUOROBENZOIC COMPOUNDS WITH 5-HT$_2$- AND $\alpha_1$-ANTAGONISTIC ACTIVITIES The present invention relates to new 4-fluorobenzoyl compounds, to processes for preparing them and to pharmaceutical compositions containing them.

Many 4-fluorobenzoic compounds derived from piperidine or pyrrolidine possess advantageous pharmacological properties and are described in the literature. In effect, 4-(4-fluorobenzoyl)-l-alkylpiperidines which are benzimidazolone, quinazoline, pyrido[1,2-a]pyrimidinone, thiadiazolo[3,2-a]pyrimidinone and pyrimido [2,1-b][1,3]thiazinone derivatives are known to be serotonin antagonists (U.S. Pat. No. 4,254,127, patent applications Ser. No. EP 013,612, EP 037,265, EP 070,053, EP 184,258). These compounds find their applications in therapy as antivasospastic and aggregation-inhibitory agents or as psychotropics. [4-(4-Fluorobenzoyl)piperidino]alkyltheophylline compounds having antiserotonin, antihistaminic and beta-stimulatory properties are described in the literature (patent application Ser. No. EP 071,738). 4-(4-Fluorobenzoyl) piperidinoalkylindols possessing antihypertensive, analgesic and tranquillizing properties (U.S. Pat. No. 4,110,459 and patent application Ser. Nos. EP 045,024 and EP 046,179) and polyalkoxyphenylpyrrolidone derivatives substituted with a 4-(4-fluorobenzoyl)-piperidine group and having vasodilator and hypotensive properties are also known (patent application Ser. No. EP 008,645). Some imides derived from 4-(4-fluorobenzoyl)piperidine or 2-[4-(4-fluorobenzoyl) piperidino]benzodioxane compounds are neuroleptic agents (patent application Ser. No. EP 261,688 and U.S. Pat. No. 4,129,655). Other [4-(4-fluorobenzoyl)-piperidino]piperidine derivatives which are usable for the treatment of dementia and the sequelae of cerebrovascular diseases are described in patent application Ser. No. EP 229,391.

Hydroxypropoxythiazole compounds or hydroxypropoxyphenyl compounds, as well as compounds of pyrimidine substituted with a 4-fluorobenzoic group, are endowed with $\alpha_1$-adrenergic and/or antihypertensive properties (U.S. Pat. No. 4,616,017, U.S. Pat. No. 4,539,318 and patent application Ser. No. DE 3,601,731). A few 4-fluorophenacylpyrrolidine derivatives are also described as being active with respect to the central nervous system (Chem. Pharm. Bull., (1977), 25(8), p. 1911).

The compounds of the present invention are distinguished from other 4-fluorobenzoic derivatives described in the literature by their original structures and by their novel pharmacological properties.

The compounds of the invention combine potent 5-HT$_2$ antagonist properties with $\alpha_1$ antagonist properties which make them especially useful in the treatment of hypertension or of conditions secondary to hypertension while providing for protection of the vascular wall. Furthermore, the compounds of the invention are capable of specifically antagonizing complex symptoms induced in animals by the injection of 5-hydroxytryptophan, which leads to the prediction that these new compounds are also serotonin antagonists at the 5-HT$_1$ type receptor level. They can hence be useful in the treatment of anxiety. The compounds of the invention additionally possess antihistaminic properties, and also find their application as antiallergic agents.

The subject of the present invention is, more especially, the 4-fluorobenzoic derivatives of formula I:

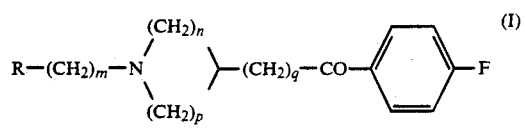

in which:
m represents an integer from 2 to 4,
n and p, which may be identical or different, each represent an integer from 1 to 3,
q represents 0 or 1, and
R represents.
either a group of formula (A):

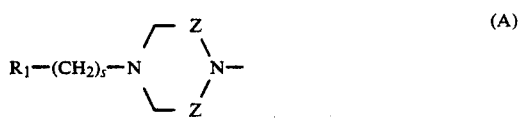

in which s represents an integer from 0 to 4, Z represents a methylene radical or a carbonyl radical and R$_1$ represents either a phenyl radical (optionally substituted with one or more halogen atoms or with a linear or branched lower alkyl radical containing from 1 to 5 carbon atoms or a lower alkoxy radical containing from 1 to 5 carbon atoms), or a diphenylmethylene radical (optionally substituted with one or more halogen atoms or with a lower alkyl radical or lower alkoxy radical), or an unsaturated five- or six-membered ring containing one or two nitrogen atoms,
or a radical of the formula (B):

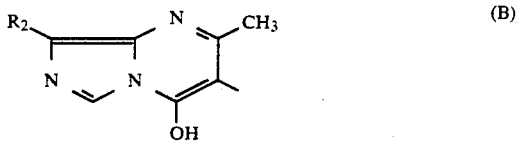

in which R$_2$ represents a carbamoyl radical, a cyano radical, a carboxy radical or an alkoxycarbonyl radical containing from 2 to 7 carbon atoms,
or a 2,4-dioxo-1,2,3,4-tetrahydroquinazolinyl radical on condition, however, that, in this case, n and p do not simultaneously represent the number 2,
or a 1-oxophthalazinyl radical,
or a 5-oxothiazolo[3,2-a]pyrimidinyl radical (optionally substituted with one or more halogen atoms or with a linear or branched alkyl radical containing from 1 to 5 carbon atoms or a lower alkoxy radical containing from 1 to 5 carbon atoms),
or a benzhydryloxy group (in which the phenyl radicals are optionally substituted with one or more halogen atoms or with a linear or branched alkyl radical containing from 1 to 5 carbon atoms or an alkoxy radical containing from 1 to 5 carbon atoms),
or a group of formula C:

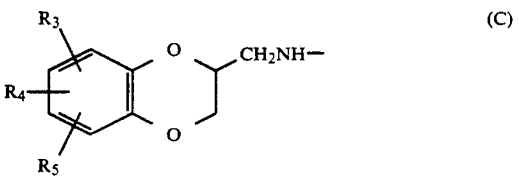

in which $R_3$, $R_4$ and $R_5$, which may be identical or different, each represent a halogen atom, an alkoxy radical having 1 to 5 carbon atoms or a linear or branched alkyl radical having 1 to 5 carbon atoms, their possible stereoisomers and their addition salts with a pharmaceutically acceptable inorganic or organic acid.

The subject of the present invention is also a process for preparing compounds of general formula I, wherein:
either
a compound of general formula II:

$$R-(CH_2)_m-X \quad (II)$$

in which R and m have the same meaning as for the formula I and X represents a leaving group such as a halogen atom, a mesyl radical or a tosyl radical,
is condensed with an amine of general formula III

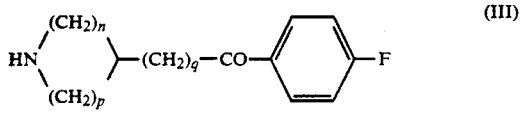

in which n, p and q have the meaning stated above for the formula I,
or
a compound of general formula IV:

$$RH \quad (IV)$$

in which R has the same meaning as for the formula I, is condensed with a compound of formula V:

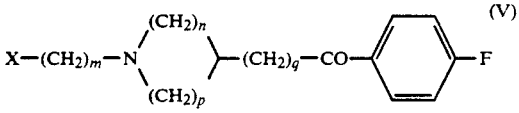

in which the meaning of m, n, p and q is identical to that given for the formula I and X represents a leaving group whose definition is identical to that given for the general formula II,
to form the compounds of formula I,
or
a 4-aminoimidazole derivative is cyclized with a compound of formula VI:

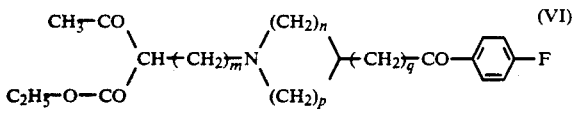

in which m, n, p and q have the meaning given for the formula I,
to form the compounds of the formula I,
in which R represents a radical of formula B and m, n, p and q have the meaning stated for the formula I,
which compounds are then,
if so desired, separated into their possible stereoisomers and/or salified with a pharmaceutically acceptable organic or inorganic acid to form the corresponding addition salts.

The compounds of general formula IV, when R represents a group of formula A, are either commercial products or products whose preparation is already known (patent application Ser. No. EP 262,993).

The compounds of general formula II, when R represents a group of formula A, are obtained by treating the corresponding compounds of general formula IV, either with a bromochloroalkane of formula VII:

$$Br(CH_2)_mCl \quad (VII)$$

in which m has the same meaning as for the formula I, or with a halohydrin of formula VIII:

$$Hal(CH_2)_mOH \quad (VIII)$$

in which m has the same meaning as for the formula I and Hal represents a halogen atom. The alcohols thereby obtained are then converted to derivatives of formula II by conventional methods.

The compounds of general formula II, when R represents a group of formula B and m is equal to 2, are obtained according to the method described in J. Heterocycl. Chem., 1974, 11, p. 873, by the condensation of 4-amino-5-carbamoylimidazole with 3-acetyldihydro-2(3H)-furanone. The alcohol derived from this reaction is then converted to the chloro derivative by the action of phosphorus oxychloride. This treatment also converts the carbamoyl radical ($R_2$) to nitrile.

3-(2-Chloroethyl)-1,2,3,4-tetrahydro-2,4-quinazolinedione is a commercial product (Janssen ®).

When R represents a benzhydryloxy group, the compounds of formula II are obtained according to the synthesis process described in Organic Synthesis Collect. Vol. IV, Wiley Ed, N.Y., 1963, p. 72, or according to the method described in J. Med. Chem., 1980, 23, p. 149.

The compounds of formula II, when R represents a group of formula C, are obtained according to the method described in J. Med. Chem., 1965, 8, p. 446.

Some amines of general formula III are already described in the literature (U.S. Pat. No. EP 13,612 and Chem. Pharm. Bull., 1977 25, p. 1911).

The amine of formula III, when n is equal to 3, p equal to 1 and q equal to 1, may also be prepared from 3-chloromethyl-l-methylpiperidine and 4-fluorobenzonitrile. The compound derived from this reaction is then demethylated according to known processes to give the expected secondary amine.

The amine of formula III, when n is equal to 3, p equal to 2 and q equal to zero, is prepared from 4-(N,N-dimethylamino)butyronitrile. This compound is condensed with 3-chloro-l-iodopropane to form 2-[2-(N,N-dimethylamino) ethyl]-5-chloropentanenitrile which, after cyclization, gives 4-cyano-l-methylperhydroazepine. From this compound and using conventional methods, the expected amine is obtained.

The compound of formula III, when n and p are equal to 1 and q is equal to 1, is prepared from ethyl cyanoacetate and 2-chloro-4-fluoroacetophenone. The ethyl 2-(4-fluorophenacyl)cyanoacetate thereby obtained is then reacted with anhydrous ethylene glycol to obtain 2-[2-(2-cyanoethoxycarbonyl) ethyl]-2-(4-fluorophenyl)-1,3-dioxolane. Hydrogenation of the latter compound leads to 2-[2-(2-aminomethylethoxycarbonyl)ethyl]-2-(4-fluorophenyl)-1,3-dioxolane, which is reacted with methylmagnesium iodide to obtain 2 (4-fluorophenyl)-2-[(2-oxo-azetidin-3-yl) methyl]dioxolane. This compound is subjected to the action of lithium aluminum hydride to obtain the expected compound.

The compounds of formula V are obtained by treating the amines of formula III, either with a bromochloroalkane of formula VII, or with a halohydrin of formula VIII. In the latter case, the alcohols obtained are converted to derivatives of formula V by conventional methods.

The compounds of formula VI are prepared by condensation of the compounds of formula V with ethyl acetoacetate (Ann. Rep. Sankyo Res. lab., (1977), 29, p. 75-98).

The condensation of the compounds of formula III or IV with the compounds II or V is carried out in a polar organic solvent in the presence of inorganic salts such as sodium carbonate and sodium iodide at a temperature of between 40° C. and 120° C.

The cyclization of the 4-aminoimidazole compounds with the compounds of formula VI is performed in the heated state and in the presence of phosphoric acid.

Among pharmaceutically acceptable acids for the preparation of addition salts with the compounds of general formula I, there may be mentioned hydrochloric, phosphoric, fumaric, citric, oxalic, sulfuric, ascorbic, tartaric, maleic, mandelic and methanesulfonic acids, and the like.

The compounds of the present invention possess highly advantageous pharmacological properties. Pharmacological tests have demonstrated their antagonist activities at the 5-HT$_2$ and $\alpha_1$ receptor level. Some compounds having potent antiserotonin properties, and especially ketanserin, possess platelet aggregation-inhibitory, anti-vasospastic and vasoprotective activities of the greatest value. However, those compounds are devoid of $\alpha_1$ antagonist activity. The 5-HT$_2$ properties combined with $\alpha_1$ antagonist properties make the compounds of the invention especially useful in the treatment of hypertension or of conditions secondary to hypertension while providing for protection of the vascular wall.

The compounds of the invention are also potent inhibitors of the complex and characteristic symptoms induced in animals by the injection of 5-hydroxy tryptophan. The compounds of the present invention are hence also serotonin antagonists at the 5-HT$_1$ type receptor level (J. Ph. Ex. Ther. (1984) 228, No. 1, p. 133-139). By virtue of their properties as antagonists at serotonin receptors at central level, and most especially 5-HT$_2$ and 5-HT$_1$ receptors, the compounds of the invention may be used for counteracting certain adverse effects of these mediators. They hence find their application more especially in anxiety and dysthymia (Ceulemans D.L.S., Hoppenbrouwers M. L., Gelders Y.G., Reyntjens A.K.M., Pharmacopsychiat., (1985) 18, p. 303-305 and Le Bars, Neuronal Serotonin Eds Osborne. N.N. and Hamon M., John Wiley and Sons Ltd, N.Y., (1988), p. 171-229), in depression and stress (Anisman H. and Zacharko R. M., Behav. Brain. Scienc., (1982), 5, p. 89-137 and Blier P., de Montigny C. and Chaput Y., J. Clin. Psychopharmacol., (1987), 7, p. 245-335), the treatment of pain (Jacobs B. L. and Trulson M. E., TINS, (1979), Novem., p. 276-280), memory disorders (Markianos M., Hadjikonstantinou and Bistolaki E., Acta Neurol. Scand., (1982), 66, p. 267-275), Parkinson's disease (Le Bars, Neuronal Serotonin Eds. Osborne NN and Hamon M, John Wiley and Sons Ltd N.Y., (1988), p. 171-229) and schizophrenia (Borison R. L., Havdala H. S. and Diamond B. I., Comms. Psychopharmacol , (1978), p. 209-214 and Iversen S. D., Neuropharmacol., (1984), 23, p. 1553-1560).

The compounds of the invention also possess antihistaminic properties. They may hence be used as antiallergic and antipruritic agents, for treatment of the airways such an rhinitis and hay fever, and for the treatment of asthma and Quincke's edema.

The invention also covers pharmaceutical compositions containing, as active principle, at least one compound of the general formula I, or one of its salts with a pharmaceutically compatible inorganic or organic acid, in combination with one or more suitable inert excipients.

The pharmaceutical compositions thereby obtained are advantageously presented in various forms such as, for example, tablets, dragees, hard gelatin capsules, suppositories, injectable solutions or solutions taken by mouth.

The dosage can vary widely in accordance with the patient's age and weight and the nature and severity of the condition, as well as the administration route. Generally speaking, the unit dosage will range between 0.5 and 100 mg and the daily dosage, usable in human therapy, between 0.5 mg and 300 mg.

The preferred administration route is the oral or parenteral route.

The examples which follow, given without implied limitation, illustrate the invention.

The melting points were measured according to the micro-Kofler technique.

The proton nuclear magnetic resonance ($^1$H NMR) or carbon-13 nuclear magnetic resonance ($^{13}$C NMR) spectra of the compounds of general formula I were recorded, depending on the case, at 60, 200 and 400 MHz, and are indicated in Table I.

EXAMPLE 1

8-Cyano-3-{2-[4-(4-fluorobenzoyl)piperidino]ethyl}-4-hydroxy-2-methylimidazo[1,5-a]pyrimidine hydrochloride

Stage A

8-Carbamoyl-4-hydroxy-3-(2-hydroxyethyl)-2-methylimidazo[5-a]pyrimidine 3 g of 4-amino-5-carbamoylimidazole hydrochloride, 1.51 g of sodium acetate, 1.69 g of ethanol, 7 g of 3-acetyl-2-tetrahydrofuranone and 45 ml of toluene are introduced successively into a three-necked flask. The mixture is heated to reflux for 90 hours. After cooling, the precipitate formed is taken up with boiling ethanol. The residue is filtered off and taken up in boiling water, and the residue is filtered off, washed with ethanol and then dried.

Yield: 62%

Proton nuclear magnetic resonance spectrum (400 MHz, solvent DMSO-d$_6$): 2.5 ppm,s,3H; 2.6 ppm,t,2H; 3.5 ppm,q, 2H; 4.6 ppm,t,1H; 7.1-7.4 ppm,m,2H; 8.1 ppm,s,1H; 11.4 ppm,m,1H

Stage B 3-(2-Chloroethyl)-8-cyano-4-hydroxy-2-methylimidazo-[1,5-a]pyrimidine 0.17 mole of the compound obtained in Stage A, dissolved in 200 ml of phosphorus oxychloride, is brought to 85° C. for one hour 30 minutes. The phosphorus oxychloride is then removed by evaporation under vacuum. 100 ml of water are added and the pH is adjusted to 7 using sodium bicarbonate, to crystallize the expected compound. The product is filtered off.

Yield: 88%

Melting point 225° C.

Proton nuclear magnetic resonance spectrum (60 MHz, solvent DMSO-d$_6$):2.45 pp,s,3H; 2.9 ppm,t,2H;

3.7 ppm, t,2H; 8.15 ppm,s,1H; 13.0–13.4 ppm, 1H exchangeable.

Stage C 9.7 g of the compound obtained in the preceding stage, 9.5 g of 4-(4-fluorobenzoyl)piperidine, 23 g of sodium carbonate, 0.5 g of potassium iodide and 800 ml of 4-methyl-2-pentanone are brought to reflux. The mixture is left to react for approximately 15 hours and is then hydrolyzed in the heated state with 200 ml of water for 3 hours. The mixture is filtered while hot and the precipitate is rinsed with acetone and then ethanol.

The product is purified on a chromatographic column containing 300 g of 70–230 mesh silica, using a mixture of dichloromethane and ethanol (90:10 V/V) as eluant. The purified product is crystallized in a mixture of dichloromethane and methanol (99:1 V/V).

8-Cyano-3-(2-[4-(4-fluorobenzoyl)piperidino]-ethyl}-4-hydroxy-2-methylimidazo[1,5-a]pyrimidine hydrochloride is then formed using ethanolic hydrogen chloride.

Yield: 35%
Melting point: >260° C.

EXAMPLE 2

1-{3-[4-(4-Fluorobenzoyl)piperidino]propyl}-4-(2-fluorobenzyl) piperazine 2,6-dione hydrochloride A mixture of 8 g of 1-(3-chloropropyl)-4-(2-fluorobenzyl) piperazine 2,6-dione, 6.1 g of 4-(4-fluorobenzoyl) piperidine, 15 g of sodium carbonate, 0.1 g of potassium iodide and 250 ml of 4-methyl-2-pentanone is brought to reflux for 5 hours.

After concentration, the residue is taken up in water and extracted with benzene. The oil thereby obtained is purified by column chromatography on 350 g of 70–230 mesh silica using dichloromethane and then a 1–5% methanol gradient as eluant. 1-{3-[4-(4-Fluorobenzoyl)-piperidino]propyl}-4-(2-fluorobenzyl)piperazine 2,6-dione hydrochloride is then formed by salifying the base obtained using ethanolic hydrogen chloride.

Yield: 42%
Melting point: 238° C.

EXAMPLE 3

1-{3-[4-(4-Fluorobenzoyl)piperidino]propyl}-4-(2-pyridylmethyl) piperazine 2,6-dione hydrochloride

Stage A 1-(3-Chloropropyl)-4-(4-fluorobenzoyl)piperidine 2.7 ml of 1-chloro-3-iodopropane, dissolved in 10 ml of dimethylformamide, are added dropwise at 20° C. to a mixture of 5 g of 4-(4-fluorobenzoyl)piperidine and 3.95 ml of triethylamine in 60 ml of anhydrous dimethylformamide. The mixture is kept stirring for 20 hours at 20° C. and then concentrated under vacuum. The residue is taken up in alkalinized water (pH 9–10) and the product is extracted with dichloromethane. The oil obtained after evaporation of the organic solvent is purified on a silica column (100 g; 70–230 mesh), using a mixture of dichloromethane and methanol (99:1 V/V) as eluant.

Yield: 60%
Proton nuclear magnetic resonance spectrum (60 MHz, solvent CDCl$_3$): 1.6–3.4 ppm,m,13H; 3.6 ppm,t,2H; 7.1 ppm,t,2H; 7.8–8.1 ppm,dd,2H

Stage B

A solution of 1.86 g of 4-(2-pyridylmethyl)piperazine 2,6-dione in 30 ml of dimethylformamide is added at 20° C. to a suspension of 0.36 g of sodium hydride. The mixture is brought to 60° C. for 30 minutes and 2.7 g of 1-(3-chloropropyl)-4-(4-fluorobenzoyl)piperidine, dissolved in 30 ml of dimethylformamide, are then added, again at 20° C. The mixture is kept stirring at 20° C. for approximately 15 hours and the reaction is completed by bringing to 70° C. for 2 hours. After concentration, the residue is taken up in water and the product is extracted with benzene. The oil obtained is purified by chromatography under pressure on 280 g of b 230–400 mesh silica, eluting with a mixture of dichloromethane and methanol (93.5:6.5 V/V). The base obtained is converted to the hydrochloride in ethanol. The precipitate obtained is then filtered off.

Yield: 35%
Melting point: 192° C.

EXAMPLE 4

1-{4-[4-(4-Fluorobenzoyl)piperidino]butyl}-4-(2-fluorobenzyl) piperazine 2,6-dione hydrochloride 2.61 g of 4-(2-fluorobenzyl)-1-(4-bromobutyl)piperazine 2,6-dione, dissolved in 40 ml of dimethylformamide, are added dropwise at 20° C. to a mixture of 1.4 g of 4-(4-fluorobenzoyl)piperidine and 0.84 g of triethylamine in 50 ml of dimethylformamide. After 15 hours, stirring at 20° C., the solvent is concentrated under vacuum. The residue is taken up in water and the product is extracted with dichloromethane. The oil obtained is purified by chromatography on 210 g of 230–400 mesh silica, eluting with a mixture of dichloromethane and methanol (95:5 V/V).

The base thereby obtained is then salified with ethanolic hydrogen chloride in a mixture of ethanol and ethyl ether.

Yield: 40%
Melting point: 198° C.

EXAMPLE 5

4-(2-Fluorobenzyl)-1-{3-[3-(4-fluorophenacyl)-1-pyrrolidinyl]propyl}piperazine 2,6-dione tartrate A mixture of 2.5 g of 3-(4-fluorophenacyl)pyrrolidine, 4 g of 1-(3-chloropropyl)-4-(2-fluorobenzyl)piperazine 2,6-dione, 1.3 g of sodium carbonate, 0.1 g of potassium iodide and 70 ml of 4-methyl-2-pentanone is heated to 120° C. for 3 hours.

The mixture is concentrated, the residue is taken up with water, the product is extracted with dichloromethane and the organic phase is then dried and concentrated.

The oil obtained is purified by chromatography on 300 g of silica 60 (70–230 mesh), using a mixture of dichloromethane and methanol (98:2 V/V) as eluant.

2 g of an oil are obtained. To obtain the monotartrate, the base is salified in a mixture of ethanol and ethyl ether.

Yield: 45%
Melting point: =65° C.

EXAMPLE 6

4-(2-Fluorobenzyl)-1-{3-[3-4-fluorophenacyl)-piperidino]propyl)}piperazine 2,6-dione ditartrate

Stage A 3-(4-Fluorophenacyl)-1-methylpiperidine

25 A solution of 33.7 g of 3-chloromethyl-N-methylpiperidine in 80 ml of tetrahydrofuran is added under nitrogen to 5.55 g of magnesium suspended in 25 ml of tetrahydrofuran. The mixture is brought to reflux for 2 hours, then cooled to 10° C. and a solution containing 30.5 g of 4-fluorobenzonitrile dissolved in 100 ml of tetrahydrofuran is added. The mixture is brought to 40° C. for 3 hours and then hydrolyzed with a solution of 68 ml of hydrochloric acid (d =1.18) in 42 ml of water. The mixture is heated to reflux for 1 hour, cooled and extracted with ethyl ether. After removal of the organic phase, the aqueous phase is alkalinized (pH 9) using caustic soda solution and filtered on celite, and the aqueous phase is extracted with dichloromethane, dried over sodium sulfate and concentrated to obtain an oil.

Yield: 85%

Proton nuclear magnetic resonance spectrum (60 MHz, solvent CDCl$_3$): 1.3–2.5 ppm,m,7H; 2.25 ppm,s,3H; 2.75 ppm,m,2H; 2.90 ppm,d,2H; 7.15 ppm,m,2H; 8.0 ppm,m,2H

Stage B

1-Ethoxycarbonyl-3-(4-fluorophencayl)piperidine

A mixture of 44.5 g of the oil obtained in Stage A, 82 g (0.755 mol) of ethyl chloroformate, 20 g of sodium carbonate, 1 g of potassium iodide and 400 ml of toluene is brought to reflux for 5 hours. The mixture is then cooled, 200 ml of 1N hydrochloric acid are added and the organic phase is separated after settling has taken place. The organic phase is washed with water and then dried over anhydrous sodium sulfate. It is concentrated. The oil obtained is used in the next step.

Yield: 85%

Stage C 3-(4-fluorophenacyl)piperidine

The whole of the oil obtained in step B is brought to reflux for 2 hours 30 minutes with 250 ml of 48% strength hydrobromic acid (d =1.48). The mixture is then concentrated under vacuum, the residue is brought to pH 10–11 using caustic soda solution, the product is extracted with dichloromethane and the organic phase is dried over sodium sulfate and concentrated.

Yield: 85%

Stage D

A mixture of 2 g of 3-(4-fluorophenacyl)piperidine, 2.7 g of 1-(3-chloropropyl)-4-(2-fluorobenzyl)piperdine 2,6-dione, 1 g of sodium carbonate, 0.1 g of potassium iodide and 30 ml of 4-methyl-2-pentanone is brought to 120° C. for 4 hours.

The mixture is then concentrated, the residue is taken up in 50 ml of water, the product is extracted with dichloromethane and the organic phase is concentrated.

The oil obtained is subjected to a purification on a chromatographic column containing 250 g of silica 60 (70–230 mesh), using a mixture of dichloromethane and methanol (98:2 V/V) as eluant.

The 4-(2-fluorobenzyl)-1-{3-[3-(4-fluorophenacyl) piperidino]propyl}piperazine 2,6-dione obtained is salified by adding two equivalents of tartaric acid to an ethanolic solution of the product. The mixture is concentrated and the precipitate is taken up in ethyl ether.

Yield: 45%

Melting point: 75° C.

EXAMPLE 7

1-{3-[4-(4-Fluorobenzoyl)piperidino]propyl}-4-(2-pyrimidinyl)-piperazine dihydrochloride A mixture of 5 g of 1-(3-chloropropyl)-4-(4-fluorobenzoyl) piperidine and 3.2 g of 4-(2-pyrimidinyl)piperazine is stirred for 24 hours at room temperature in the presence of an excess of sodium carbonate in 70 ml of dimethylformamide.

The precipitate formed is removed. The solution is concentrated and the residue is taken up in 100 ml of water. This aqueous phase is extracted three times with 100 ml of dichloromethane. The organic phase is dried over anhydrous sodium sulfate and then concentrated to obtain an oily residue which crystallizes in isopropyl ether.

Yield: 25%

1-{3-[4-(4-Fluorobenzoyl)piperidino]propyl}-4-(2-pyrimidinyl) piperazine dihydrochloride is obtained after the addition of a suitable quantity of ethanolic hydrogen chloride.

Melting point: 260° C.

EXAMPLE 8

8-Carbamoyl-3-{2-[4-(4-fluorobenzoyl)piperidino]-ethyl}-4-hydroxy-2-methylimidazol[1,5-a]pyrimidine hydrochloride

Stage A 1-(2-Chloroethyl)-4-(4-fluorobenzoyl)piperidine 9 56 g of ethylene oxide are added at −10° C. to a solution of 45 g of 4-(4-fluorobenzoyl)piperidine in 500 ml of anhydrous methanol After 15 hours, stirring at 20° C. followed by 5 hours at 50° C., the reaction is almost complete. The mixture is concentrated under vacuum. The residue obtained is purifed on a chromatographic column containing 100 g of 70-230 mesh silica, using dichloromethane as eluant.

The oil obtained is dissolved in 800 ml of anhydrous benzene. 10.4 ml of thionyl chloride are added dropwise at 5° C. to this solution. The mixture is then brought to reflux for 2 hours 30 minutes. After cooling, the precipitate is filtered off. The latter is taken up in alkalinized water and the product is extracted with benzene. After evaporation, the residue obtained is purified by passage through 100 g of 70-230 mesh silica, using dichloromethane as eluant.

Yield: 41%

Proton nuclear magnetic resonance spectrum (60 MHz, solvent CDCl$_3$): 1.6–3.5 ppm,m,11H; 3.65 ppm,t,2H; 7–7.5 ppm,m,2H; 7.8–8.3 ppm,m,2H

Stage B

Ethyl 2-acetyl-4-[4-(4-fluorobenzoyl)piperidino]-butyrate

A solution of 5.45 g of ethyl acetoacetate in 20 ml of tetrahydrofuran is added at 0° C. to a suspension of 1.68 g of sodium hydride at a concentration of 60% in oil in 100 ml of anhydrous tetrahydrofuran. The medium is maintained at 20° C. for 1 hour 30 minutes. 6.3 g of sodium iodide are added, followed by the addition at 0° C. of 11.3 g of 1-(2-chloroethyl)-4-(4-fluorobenzoyl)-piperidine in 100 ml of tetrahydrofuran. The reaction mixture is brought to reflux for 15 hours. It is concentrated under vacuum. The residue is taken up in water and the product is extracted with dichloromethane.

After evaporation, the oil is purified on 300 g of 70–230 mesh silica, using a mixture of dichloromethane and methanol (99:1 V/V) as eluant.

Yield: 48%

Proton nuclear magnetic resonance spectrum (200 MHz, solvent CDCl$_3$): 1.3 ppm,t,3H; 1.5–2.5 ppm,t+s+m,2H+3H+9H; 2.8–3.0 ppm,t,1H; 4.1–4.3 ppm,q,2H; 7–7.2 ppm,t,2H; 7.9–8 ppm,dd,2H

Stage C

A homogeneous mixture containing 2.5 g of 4-amino-5-carbamoylimidazole hydrochloride, 6.15 g of the compound obtained in the preceding stage and 15 g of phosphoric acid is prepared at 20° C. This mixture is brought to 80° C. for approximately 30 minutes and then hydrolyzed with ice. The precipitate obtained is filtered. It is salified using an excess of ethanolic hydrogen chloride, bringing the mixture to reflux in an aqueous-alcoholic mixture (ethanol 800 ml+H$_2$O 60 ml). The product is filtered off after cooling.

Yield: 72%

Melting point: >300° C.

EXAMPLE 9

8-Carbamoyl-3-{2-[3-(4-fluorophenacyl)-1-pyrrolidinyl]ethyl}-4-hydroxy-2-methylimidazo[1,5-a]pyrimidine hydrochloride

Stage A 3-(4-Fluorophenacyl)-1-(2-hydroxyethyl)pyrrolidine

A mixture of 30.5 g of 3-(4-fluorophenacyl)pyrrolidine (Chem. Pharm. Bull., 1977, 25(8), p. 1911–1922), 19.4 g of 2-bromoethanol, 15.6 g of sodium carbonate and 400 ml of acetonitrile is heated to reflux for 6 hours. The mixture is concentrated, the residue is taken up in 150 ml of aqueous saline, the product is extracted 5 times with 150 ml of dichloromethane and this organic phase is dried over anhydrous sodium sulfate and concentrated. The oil obtained is purified by chromatography on 650 g of silica (70–230 mesh), using a mixture of dichloromethane, methanol and ammonia solution (96:4:0.4 V/V) as eluant. A colorless oil is obtained.

Yield: 50%

Proton nuclear magnetic resonance spectrum (60 MHz, solvent CDCl$_3$): 1.8–2.5 ppm,m,2H; 2.9–4.0 ppm,m,11H; 7.2 ppm,t,2H; 8 ppm,dd,2H

Stage B

Ethyl 2-acetyl-4-[3-(4-fluorophenacyl)-1-pyrrolidinyl]butyrate

A solution of 3.88 g of methanesulfonyl chloride is added at 0° C. to a suspension of 8.5 g of the product obtained in Stage A in 100 ml of tetrahydrofuran. The mixture is left stirring for 3 hours at 15° C., and this suspension is then added to a solution, cooled to 0° C., of 4.4 g of ethyl acetoacetate containing 1.63 g of sodium hydride in 100 ml of tetrahydrofuran. The mixture is then brought to reflux for 12 hours, hydrolyzed with 5 ml of water and concentrated, and the residue is taken up in 150 ml of dichloromethane. The organic phase is washed with 50 ml of water, dried over anhydrous sodium sulfate and concentrated. The oil obtained is purified by chromatography on 600 g of 70–230 mesh silica, using a mixture of dichloromethane and methanol (99:1 V/V) as eluant.

Yield: 50%

Proton nuclear magnetic resonance spectrum (60 MHz, solvent CDCl$_3$):1.1–1.4 ppm,t,3H; 1.4–3.2 ppm,m,11H; 2.25 ppm,s,3H; 3.15 ppm,d,2H 3.65 ppm,t,1H; 4.1–4.3 ppm,q,2H: 7.0–7.2 ppm,t,2H; 7.9–8.0 ppm,dd,2H

Stage C 7 g of the compound obtained in the preceding stage, 3.13 g of 4-amino-5-carbamoylimidazole hydrochloride and 60 g of phosphoric acid are mixed. This mixture is heated to 85° C. for 1 hour and then hydrolyzed at 5° C. with 100 g of ice and 100 ml of water. The mixture is brought to pH 12 using caustic soda solution and extracted 4 times with dichloromethane. The organic phase is concentrated The precipitate formed and the concentrate of the organic phase are dissolved in 150 ml of water at pH 12 and the solution obtained is extracted in a Jalade perforator using dichloromethane for 24 hours. A white precipitate is thereby obtained in the organic phase, and is filtered off.

This precipitate is dissolved in 180 ml of ethanol at 60° C., two equivalents of ethanolic hydrogen chloride are added and the precipitate formed is filtered off after 12 hours to obtain 8-carbamoyl-3-{2-[3-(4-fluorophenacyl)-1-pyrrolidinyl]ethyl}-4-hydroxy-2-methylimidazo[1,5-a]pyrimidine hydrochloride.

Yield: 30%

Melting point: >270° C.

EXAMPLE 10

2,4-Dioxo-3-{2-[3-(4-fluorophenacyl)-1-pyrrolidinyl]ethyl}-1,2,3,4-tetrahydrocuinazoline hydrochloride A mixture of 5.5 g of 3-(2-chloroethyl)-2,4-dioxo-1,2,3,4-tetrahydroquinazoline, 4.2 g of 3-(4-fluorophenacyl) pyrrolidine, 5.1 g of sodium hydrogen carbonate and 100 ml of toluene is brought to reflux for 12 hours. The organic phase is then washed with water and the toluene is concentrated under vacuum. The oil obtained is then purified by chromatography on 300 g of 70–230 mesh silica, using a mixture of dichloromethane and methanol (97:3 V/V) as eluant.

The corresponding hydrochloride is obtained in a mixture of ether and acetone.

Yield: 35%

Melting point: 145° C.

EXAMPLE 11

1,1-Bis(4-fluorophenyl)-4-[4-(4-fluorobenzoyl)-piperidino]-2-oxabutane maleate

Stage A 1,1-Bis(4-fluorophenyl)-4-chloro-2-oxabutane

A mixture of 0.362 mol of 4,4,-difluorobenzhydrol, 0.77 mol of 2-chloroethanol and 0.257 mol of para-toluenesulfonic acid in 500 ml of anhydrous toluene is brought to reflux. The water formed is removed using a Dean and Stark apparatus. The residue is cooled. The organic phase is washed with water, then with dilute aqueous carbonate and then again with water.

After concentration, an oil is obtained.

Yield: 99%

Proton nuclear magnetic resonance spectrum (60 MHz, solvent CDCl$_3$): 3.7 ppm,s,4H; 5.4 ppm,s,1H; 6.9–7.6 ppm,m,8H

Stage B

A mixture of 2.47 g of the compound obtained in the preceding stage, 2.07 g of 4-(4-fluorobenzoyl)piperidine, 10.6 g of sodium carbonate and 100 ml of 4-methyl-2-pentanone is brought to reflux for 4 days. After concentration the residue is taken up in dichloromethane and washed with water. The oil obtained is purified on 150 g of silica (230–400 mesh) using a mixture of dichloromethane and ethanol (99:1 V/V).

The base is then converted to the maleate in a mixture of ethyl ether and acetone and the salt obtained in recrystallized in the same mixture.

Yield: 35%
Melting point: 124° C.

EXAMPLE 12

2-Aza-1-(1,4-benzodioxan-2-yl)-5-[4-(4-fluorobenzoyl)piperidino]pentane dihydrochloride A mixture of 8.7 g of 2-methyl-1,4-benzodioxane (prepared according to the process described in J. Med. Chem. (1965), 8, p.446), 5 g of 1-(3-chloropropyl)-4-(4-fluorobenzoyl) piperidine, 1.86 g of sodium carbonate, 50 ml of acetonitrile and 60 ml of methyl ethyl ketone is brought to reflux for 48 hours.

The mixture is then concentrated, 150 ml of water are added, the product is extracted with dichloromethane and the organic phase is dried over anhydrous sodium sulfate and concentrated The 12 g of oil obtained are purified by chromatography and 400 g of Merck ® silica 60 (70–230 mesh), using a mixture of dichloromethane, methanol and ammonia solution (98:2:0.2 V/V) as eluant.

4 g of an oil are thereby recovered, the hydrochloride of which oil is prepared in acetone.

Yield: 50%
Melting point: 238°

EXAMPLE 13

8-Carbamoyl-3-{2-[3-(4-fluorophenacyl)piperidino]-ethyl}-4-hydroxy-2-methylimidazo[1,5-a]pyrimidine hydrochloride

Stage A 3-(4-Fluorophenacyl)-1-(2-hydroxyethyl)piperidine

A mixture of 28.5 g of 3-(4-fluorophenacyl)piperidine, obtained in Stage C of Example 6, 17.7 g of 2-bromoethanol, 13.7 g of sodium carbonate and 250 ml of acetonitrile is brought to reflux for 12 hours. The mixture is then concentrated, the residue is taken up in 100 ml of water and the product is extracted with dichloromethane. The organic phase is dried and concentrated.

Yield: 85%
Proton nuclear magnetic resonance spectrum (200 MHz, solvent CDCl$_3$): 0.9–2.5 ppm,m,7H; 2.5 ppm,t,2H; 2.7–2.9 ppm,m,2H; 2.8–2.9 ppm,d,2H; 3.5–3.6 ppm,t,2H; 7.0–7.2 ppm,t,2H; 8.0 ppm,dd,2H

Stage B 1-(2-Chloroethyl)-3-(4-fluorophenacyl)piperidine

A solution of 15.1 g of thionyl chloride in 20 ml of benzene is added to a solution of 30.5 g of the product obtained in the preceding stage, dissolved in 200 ml of anhydrous benzene The mixture is then brought to reflux for 3 hours and thereafter concentrated, the residue is taken up in 100 ml of water, the product is extracted with benzene and the organic phase is dried and concentrated. The oil obtained is purified by filtration on 250 g of silica (70–230 mesh), using a mixture of dichloromethane and methanol (98:2 V/V) as eluant.

Yield: 75%

Stage C

Ethyl 2-acetyl-4-[3-(4-fluorophenacyl)piperidino]-butyrate

A solution of 6.2 g of ethyl acetoacetate is added at 0° C. to a suspension of 1.13 g of sodium hydride in 150 ml of tetrahydrofuran. After 15 minutes at this temperature, 7.1 g of anhydrous sodium iodide are added, followed by the addition at 0° C. of 13.5g of the product obtained in Stage B. The mixture is then brought to reflux for 12 hours and the whole is thereafter concentrated, the residue is taken up in water and the product is extracted with dichloromethane. The 16.9 g of oil obtained are purified by chromatography on 900 g of silica (70–230 mesh), using a mixture of dichloromethane and methanol (98:2 V/V) as eluant.

Yield: 45%
Proton nuclear magnetic resonance spectrum (200 MHz, solvent CDCl$_3$): 1.3–2 5 ppm,m+s+m+m+m, 2H+3H+2H+1H+6H; 2.6–3.0 ppm,m,4H; 3.5 ppm,t,1H; 4.15 ppm,q,2H; 7.15 ppm,t,2H; 8.0 ppm,dd,2H

Stage D

A mixture of 5 g of the product obtained in the preceding stage, 1.72 g of 5-amino-4-carbamoylimidazole hydrochloride, 0.87 g of anhydrous sodium acetate and 200 ml of ethanol is brought to reflux for 60 hours in a round-bottomed flask equipped with a condenser. The precipitate formed is then filtered off.

This base is salified by dissolving it in ethanol in the heated state and adding two equivalents of ethanolic hydrochloric acid. The mixture is cooled and the precipitate obtained is filtered off to isolate the hydrochloride.

Yield: 55%
Melting point: =270° C.

EXAMPLE 14

1-{3-[4-(4-Fluorobenzoyl)piperidino]propyl}-4-(2-methylbenzyl) piperazine 2,6-dione hydrochloride This compound was prepared according to the process described in Example 3, using 4-(2-methylbenzyl)-piperazine 2,6-dione in Stage B instead of 4-(2-pyridylmethyl) piperazine 2,6-dione.

Yield: 30%
Melting point: 249° C.

EXAMPLE 15

1-{3-[4-(4-Fluorobenzoyl)piperidino]propyl}-4-(3-methylbenzyl) piperazine 2,6-dione hydrochloride This compound was prepared according to the process described in Example 3, using 4-(3-methylbenzyl) piperazine 2,6-dione in Stage B instead of 4-(2-pyridylmethyl) piperazine 2,6-dione.

Yield: 40%
Melting point: 231° C.

EXAMPLE 16

4-(4-Chlorobenzyl)-1-{3-[4-(4-fluorobenzoyl)-piperidino]propyl}piperazine 2,6-dione hydrochloride This compound was prepared according to the process described in Example 3, using 4-(4-chlorobenzyl) piperazine 2,6-dione in Stage B instead of 4-(2-pyridylmethyl) piperazine 2,6-dione.

Yield: 30%

Melting point: 239° C.

EXAMPLE 17

1-{2-[4-(4-Fluorobenzoyl)piperidino]ethyl}-4-(2-fluorobenzyl) piperazine 2,6-dione hydrochloride This compound was prepared from 1-(2-chloroethyl)-4-(4-fluorobenzoyl)piperidine and 4-(2-fluorobenzyl) piperazine 2,6-dione according to the process described in Example 3, Stage B.
Yield: 31%
Melting point: 197° C.

EXAMPLE 18

1-{3-[4-(4-Fluorobenzoyl)piperidino]propyl}-4-(3-methoxybenzyl) piperazine 2,6-dione hydrochloride This compound was prepared according to the process described in Example 3, using 4-(3-methoxybenzyl) piperazine 2,6-dione in Stage B instead of 4-(2-pyridylmethyl)piperazine 2,6-dione.
Yield: 45%
Melting point: 202° C.

EXAMPLE 19

4-[(4-Chlorophenyl)phenylmethyl]-1-{2-[4(4-fluorobenzoyl) piperidino]ethyl}piperazine 2.6-dione hydrochloride This compound was prepared from 1-(2-chloroethyl)-4-(4-fluorobenzoyl)piperidine and 4-[(4-fluorophenyl) phenylmethyl]piperazine 2,6-dione according to the process described in Example 3, Stage B.
Yield: 55%
Melting point: 180° C.

EXAMPLE 20

1-{3-[3-(4-Fluorophenacyl)-1-pyrrolidinyl]propyl}-4-(2-pyrimidinyl)piperazine trihydrochloride This compound was prepared according to the process described in Example 5, using 1-(3-chloropropyl)-4-(2-pyrimidinyl)piperazine instead of 1-(3-chloropropyl)-4-(2-fluorobenzyl)piperazine 2,6-dione.
Yield: 45%

EXAMPLE 21

4-{2-[4-(4-Fluorobenzoyl)piperidino]ethyl}-1-(2-pyrimidinyl) piperazine dihydrochloride This compound was prepared from 1-(2-chloroethyl)-4-(4-fluorobenzoyl)piperidine and 1-(2-pyrimidinyl) piperzine according to the process described in Example 3, Stage B.
Yield: 30%
Melting point: >260° C.

EXAMPLE 22

8-Carbamoyl-3-{3-[4-(4-fluorobenzoyl)piperidino]propyl}-4-hydroxy-2-methylimidazo[1,5-a]pyrimidine hydrochloride This compound was prepared according to the process described in Example 8, but using 1-(3-chloropropyl)-4-(4-fluorobenzoyl)piperidine in Stage B instead of 1-(2-chloroethyl)-4-(4-fluorobenzoyl)piperidine
Yield: 60%
Melting point: >260° C.

EXAMPLE 23

4-[4-(4-Fluorobenzoyl)piperidino]-1-[(4-fluorophenyl) phenyl]-2-oxabutane maleate This compound was synthesized according to the process described in Example 11, using 4-fluorobenzhydrol in Stage A instead of 4,4,-difluorobenzhydrol.
Yield: 38%
Melting point: 136° C.

EXAMPLE 24

1-{2-[4-(4-Fluorobenzoyl)piperidino]ethyl}-4-(2-pyridylmethyl) piperazine 2,6-dione trihydrochloride This compound was prepared according to the process described in Example 3, Stage B, but using 1-(2-chloroethyl)-4-(4-fluorobenzoyl)piperidine instead of 1-(3-chloropropyl)-4-(4-fluorobenzoyl)piperidine.
Yield: 79%
Melting point: 160° C.

EXAMPLE 25

4-[4-(4-Fluorobenzoyl)piperidino]-1-[(2-fluorophenyl) phenyl]-2-oxabutane maleate This compound was synthesized according to the process described in Example 11, using 2-fluorobenzhydrol in Stage A instead of 4,4,-difluorobenzhydrol.
Yield: 35%
Melting point: 132° C.

EXAMPLE 26

4-[4-(4-Fluorobenzoyl)piperidino]-1-[(4-methoxyphenyl) phenyl]-2-oxabutane maleate This compound was synthesized according to the process described above, using 4-methoxybenzhydrol.
Yield: 35%
Melting point: 132° C.

EXAMPLE 27

8-Cyano-3-{2-[4-(4-fluorobenzoyl)perhydro-1-azepinyl]ethyl}-4-hydroxy-2-methylimidazo[1,5-a]pyrimidine hydrochloride

Stage A 4-(N,N-Dimethylamino)butyronitrile 420 g of dimethylamine are added to a solution, heated to 80° C., of 400 g of 4-chlorobutyronitrile in 1,200 ml of pure ethanol After 12 hours under reflux, the solvent is concentrated, 3 liters of ethyl ether are then added and the precipitate formed is removed The filtrate is concentrated and distilled at 12 mm Hg.
Proton nuclear magnetic resonance spectrum (200 MHz, solvent $CDCl_3$): 1.75 ppm,q,2H; 2.25 ppm,s,6H; 2.3–2.5 ppm,t+t,2H+2H

Stage B

2-[2-(N,N-Dimethylamino)ethyl]-5-chloropentanenitrile

A solution of 0.800 mol of the product obtained in the preceding stage is added to a solution, cooled to −85° C., of 0.800 mol of lithium diisopropylamide in 600 ml of tetrahydrofuran. The mixture is left at −85° C. for 20 minutes, and 0.800 mol of pure 3-chloro-1-iodopropane is then added in the course of 5 minutes. The mixture is left stirring for one hour and is then hydrolyzed at −80° C. with 500 ml of 3% strength acetic acid. The mixture is concentrated under vacuum, the residue is taken up in 250 ml of water, the product is extracted with dichloromethane and this extract is concentrated.

Yield: 90%

Proton nuclear magnetic resonance spectrum (200 MHz, solvent CDCl$_3$): 1.6–2.1 ppm,m,6H; 2.2 ppm,s,6H; 2.3–2.6 ppm,m,2H; 2.75 ppm,m,1H; 3.6 ppm,t,2H

Stage C

4-Cyano-1-methylperhydroazepine

A mixture of 140 g of the above product and 850 ml of nitrobenzene is brought to 120° C. for 12 hours and then cooled to 15° C., and 2 liters of ethyl ether are added. The precipitate obtained is filtered off and rinsed with ether. The product obtained is then mixed with one liter of decanol and the mixture is brought to reflux for two hours. It is then cooled and extracted four times with 500 ml of 1N hydrochloric acid, and this extract is neutralized with sodium hydroxide and extracted with dichloromethane. The oil is distilled under vacuum.

Yield: 70%

Proton nuclear magnetic resonance spectrum (200 MHz, solvent CDCl$_3$): 1.5–2.2 ppm,m,6H; 2.35 ppm,s,3H; 2.5–3.0 ppm,m+m, 1H+4H

Stage D

4-(4-Fluorobenzoyl)-1-methylperhydroazepine

A solution of 0.0725 mol of the amine obtained in Stage C is added at 20° C. to a solution of 0.143 mol of 4-fluorophenylmagnesium bromide in 150 ml of ethyl ether. The reaction medium is brought to reflux for 5 hours, then left for 12 hours at room temperature and thereafter hydrolyzed with 40 ml of concentrated hydrochloric acid and 25 ml of water. The mixture is brought to reflux for 1 hour 30 minutes and cooled, the ether is decanted and the aqueous phase is alkalinized and extracted with dichloromethane. The oil obtained is purified by crystallization of the corresponding oxalate.

Yield: 60%

Proton nuclear magnetic resonance spectrum (200 MHz, solvent CDCl$_3$):1: 1.65–2.20 ppm,m,6H; 2.5–2.8 ppm,m,4H; 3.4 ppm,s,3H; 3.6 ppm,m,1H; 7.1 ppm,dd,2H; 7.95 ppm,t,2H

Stage E

4-(4-Fluorobenzoyl)-1-ethoxycarbonylperhyiroazepine

Carbamoylation of the amine obtained in Stage C is performed according to the procedure described in step B of Example 6. The compound obtained is then purified by column chromatography.

Yield: 65%

Proton nuclear magnetic resonance spectrum (200 MHz, solvent CDCl$_3$): 1.25 ppm,t,3H; 1.5–2.2 ppm,m,6H, 3.05–3.9 ppm,m,5H; 4.15 ppm,q,2H; 7.1 ppm,t,2H; 7.9–8.1 ppm,dd,2H

Stage F

4-(4-Fluorobenzoyl)perhydroazepine

This compound was obtained from 4-(4-fluorobenzoyl)-1-ethoxycarbonylperhydroazepine using hydrobromic acid according to the procedure described in Stage C of Example 6. The amine obtained is used in Stage G without purification.

Stage G

The compound obtained in Stage F, 9.7 g of 3-(2-chloroethyl)-8-cyano-4-hydroxy-2-methylimidazo[1,5-a]-pyrimidine, 23 g of sodium carbonate, 0.5 g of potassium iodide and 800 ml of 4-methyl-2-pentanone are brought to reflux. The procedure then adopted is as described in Example 1, Stage C, to obtain the expected hydrochloride.

Yield: 35%

Melting point: >260° C.

EXAMPLE 28

8-Cyano-3-{2-[3-(4-fluorophenacyl)-1-pyrrolidinyl]-ethyl}-4-hydroxy-2-methylimidazo[1,5-a]pyrimidine hydrochloride A mixture of 3.2 g of 8-carbamoyl-3-{2-[3-(4-fluorophenacyl)-1-pyrrolidinyl]ethyl}-4-hydroxy-2-methylimidazo[1,5-a]pyrimidine and 20 ml of phosphorus oxychloride is brought to 85° C. for 3 hours. It is then concentrated under vacuum, the residue is taken up in water and the mixture is neutralized with sodium carbonate solution and extracted five times with chloroform. The solid obtained is purified by chromatography on 70–230 mesh silica, using a mixture containing dichloromethane, methanol and ammonia solution (95:5:0.5 V/V/V) as eluant.

The corresponding hydrochloride is obtained in an ether/ethanol mixture.

Yield: 20%

Melting point: 170° C.

EXAMPLE 29

2,4-Dioxo- 3-{2-[4-(4-fluorobenzoyl)perhydro-1-azepinyl]ethyl}-1,2,3,4-tetrahydroquinazoline hydrochloride This compound was prepared according to the process described in Example 10, using 4-(4-fluorobenzoyl) perhydroazepine in place of 3-(4-fluorophenacyl)pyrrolidine.

Yield: 60%

Melting point: 238° C.

EXAMPLE 30

8-Carbamoyl-3-{2-[4-(4-fluorobenzoyl)perhydro-1-azepinyl]ethyl}-4-hydroxy-2-methylimidazo[1,5-a]pyrimidine hydrochloride This compound was synthesized according to the process described in Example 9, using 4-(4-fluorobenzoyl) perhydroazepine instead of 3-(4-fluorophenacyl)-pyrrolidine in Stage A.

Yield: 25%

Melting point: >260° C.

EXAMPLE 31

2-{2-[3-(4-Fluorophenacyl)-1-pyrrolidinyl]ethyl}-1-oxophthalazine hydrochloride

Stage A

2-{2-[(Tetrahydro-2-pyranyl)oxy]ethyl}-1-oxophthalazine

A solution of 41.5 g of potassium hydroxide in 53 ml of water is added at room temperature to a solution of 61 g of 1-oxophthalazine in 430 ml of dimethyl sulfoxide. After 30 minutes, 130 g of tetrahydro-2-pyranyl 2-bromoethyl ether are added to the suspension obtained. The mixture is left stirring for 30 hours at room temperature and then concentrated, the residue is taken up in 400 ml of water and the product is extracted with dichloromethane. The organic phase is concentrated.

Yield: 80%

Proton nuclear magnetic resonance spectrum (400 MHz, solvent CDCl$_3$): 1.3 to 2 ppm,m,6H; 3.3 to 4.8 ppm,m+m, 1H+6H; 7.6 to 7.9 ppm,m,3H; 8.15 ppm,s,1H; 8.4 ppm,m,1H

Stage B

2-(2-Hydroxyethyl)-1-oxo-2H-phthalazine

A mixture of 91 g of the product obtained in Stage A, 500 ml of acetic acid, 250 ml of tetrahydrofuran and 150 ml of water is heated to 55° C. for 15 hours. The mixture is then concentrated at 1 mm Hg and the oil obtained is purified by chromatography on 70-230 mesh silica, using a dichloromethane/methanol/ammonia solution mixture (99:1:0.1 V/V/V) as eluant.

Yield: 75%

Proton nuclear magnetic resonance spectrum (200 MHz, solvent CDCl$_3$): 4.0 ppm,q,2H; 4.9 ppm,t+t,1H+3H; 7.75 ppm,m,3H; 8.2 ppm,s,1H; 8.35 ppm,d,1H

Stage C

2-(2-Chloroethyl)-1-oxo-2H-phthalazine

A mixture of 45 g of the product obtained in Stage B, 31 g of thionyl chloride and 350 ml of chloroform is brought to reflux for 3 hours. The mixture is concentrated, the residue is taken up in ethyl ether and the solid obtained is filtered off.

Yield: 70%

Proton nuclear magnetic resonance spectrum (200 MHz, solvent CDCl$_3$): 3.95 ppm,t,2H; 4.6 ppm,t,2H; 7.15 to 7.9 ppm,m,3H; 8.2 ppm,s,1H; 8.4 ppm,m,1H

Stage D

A mixture of 8 g of the product obtained in Stage C, 10 g of 3-(4-fluorophenacyl)pyrrolidine, 8.8 g of sodium hydrogen carbonate and 200 ml of methylbenzene is brought to reflux for 30 hours. The mixture is then filtered and concentrated. The oil obtained is purified by chromatography on 70-230 mesh silica, using a dichloromethane/methanol/ammonia solution mixture (98.5:1.5:0.15 V/V/V) as eluant.

The 9.3 g of base thereby obtained are salified in acetone with ethanolic hydrochloric acid.

Yield: 60%

Melting point: 182° C.

EXAMPLE 32

2.4-Dioxo-3-{2-[3-(4-fluorophenacyl)-1-azetidinyl]-ethyl}-1,2,3,4-tetrahydroquinazoline

Stage A

Ethyl 2-(4-fluorophenacyl)cyanoacetate

A solution of 86.7 g of sodium in 4,500 ml of anhydrous ethanol is added at 15° C. to a solution of 528 g of ethyl cyanoacetate in 500 ml of anhydrous ethanol. After one hour, the mixture is cooled to 0° C. and a solution of 620 g of 2-chloro-4-fluoroacetophenone in one liter of ethanol is added to the solution obtained. The reaction mixture is left for 12 hours at room temperature, then hydrolyzed with 200 ml of water and concentrated. The residue is taken up in one liter of water and this aqueous phase is neutralized to pH 7 and extracted with dichloromethane, followed by concentration.

The oil obtained is distilled at 0.06 mm Hg.

Yield: 88%

Melting point: 160°-180° C.

Proton nuclear magnetic resonance spectrum (200 MHz, solvent DMSO-d$_6$): 1.0-1.3 ppm,t,3H; 3.8 ppm,d,2H; 4-4.3 ppm,q,2H: 4.55 ppm,t,1H; 7.4 ppm,t,2H; 8.1 ppm,dd,2H.

Stage B

2-[2-(2-Cyanoethoxycarbonyl)ethyl]-2-(4-fluorophenyl)-1,3-dioxolane

The mixture of 906 g of ethyl 2-(4-fluorophenacyl)cyanoacetate, 2,700 ml of anhydrous ethylene glycol, 1,300 ml of ethyl orthoformate and 20 g of methanesulfonic acid is heated to 95° C. The ethanol and ethyl formate which form are distilled off. After 72 hours, the reaction mixture is cast into 10 liters of a solution containing 200 g/l of sodium carbonate and the product is extracted with ethyl ether. The oil obtained is purified by chromatography on 70-230 mesh silica, using a cyclohexane/ethyl ether mixture (85:15 V/V) as eluant.

Yield: 75%

Proton nuclear magnetic resonance spectrum (200 MHz, solvent CDCl$_3$): 1: 1.2-1.4 ppm,t,3H; 2.4-2.7 ppm,m,2H; 3.7-3.9 ppm,m,3H; 4.0-4.2ppm,m,2H; 4.2-4.4 ppm,q,2H; 7-7.15 ppm,t,2H; 7.4-7.5 ppm,dd,2H

Stage C

2-{2-[2-(Aminomethyl)ethoxycarbonyl]ethyl}-2-(4-fluorophenyl)-1,3-dioxolane A Parr apparatus is charged with 450 g of the product obtained in Stage B, 900 ml of acetic acid, 3,000 ml of anhydrous ethanol and 20 g of platinum oxide. The mixture is hydrogenated at 5 bars at 45° C. When the theoretical volume has been absorbed, the catalyst is filtered off and the solvent is evaporated off under vacuum. The residue is taken up in 1 liter of water and the mixture is neutralized with sodium hydroxide and extracted with dichloromethane. The oil obtained is purified by chromatography on 70-230 mesh silica, using a mixture of dichloromethane, methanol and ammonia solution (95:5:0.5 V/V/V) as eluant.

Yield: 60%

Proton nuclear magnetic resonance spectrum (200 MHz, solvent CDCl$_3$): 2 ppm,dd,1H; 2.35 ppm,dd,1H; 2.6 ppm,m,1H; 2.8 ppm,m,2H; 3.7 ppm,m,2H; 4.1 ppm,q,2H; 4.1 ppm,d,2H; 7 ppm,m,2H; 7.4 ppm,m,2H

Stage D

2-(4-Fluorophenyl)-2-[(2-oxo-azetidin-3-yl)-methyl]-dioxalane

A solution of 150 g of the product obtained in Stage C in 150 ml of ethoxyethane is added at 0° C. to a solution of 2 mol of methylmagnesium iodide in 650 ml of ethoxyethane. After 4 hours at this temperature, the reaction mixture is hydrolyzed with 250 ml of saturated ammonium chloride solution. After settling has taken place, the organic phase is separated and concentrated. The oil obtained is purified by chromatography on 70-230 mesh silica. Eluant dichloromethane/methanol/ammonia solution (98:2:0.2 V/V/V).

Yield: 72%

Proton nuclear magnetic resonance spectrum (200 MHz, solvent CDCl$_3$): 2.1 ppm,dd,1H; 2.5 ppm,dd,1H; 3.05 ppm,m,1H; 3.35 ppm,m,2H; 3.75 ppm,m,2H; 4.0 ppm,m,2H; 5.75 ppm,m,1H; 7.0 ppm,t,2H; 7.4 ppm,dd,2H

Stage E 2-(4-Fluorophenyl)-2-[(azetidin-3-yl)-methyl]-dioxalane

A solution of 15 g of the product obtained in Stage D in 150 ml of tetrahydrofuran is added at −20° C. to a suspension of 4.6 g of lithium aluminum hydride in 150 ml of anhydrous ethoxyethane. The mixture is then brought to reflux for 12 hours and thereafter hydrolyzed with 80 ml of water and 10 ml of 10% strength sodium hydroxide solution. The oil obtained is purified by chromatography on 70–230 mesh silica, using a mixture of dichloromethane, methanol and ammonia solution (90:10:1 V/V/V) as eluant.

Yield: 78%

$^{13}$C nuclear magnetic resonance spectrum (400 MHz, solvent DMSO-d$_6$): 30.1 ppm; 44.2 ppm, 52.4 ppm, 64.02 ppm; 108.9 ppm; 114.7 ppm; 127.4 ppm; 138.5 ppm; 161.4 ppm

Stage F 2,4-Dioxo-3-{-2-[3-[2-(4-Fluorophenyl)-2-methylene-1,3-dioxolane]-1-azetidinyl]ethyl}-1,2,3,4-tetrahydroquinazoline A mixture of 11 g of the product obtained in Stage E, 10.5 g of 3-(2-chloroethyl)-2,4-dioxo-1,2,3,4-tetrahydroquinazoline, 6.5 g of sodium carbonate and 150 ml of toluene is brought to reflux for 15 hours. The mixture is filtered, the precipitate is rinsed with dichloromethane and the filtrate is concentrated. The solid residue obtained is taken up in an ethoxyethane/ethyl acetate mixture and the precipitate is filtered off.

Yield: 70%

Melting point: 185° C.

Proton nuclear magnetic resonance spectrum (200 MHz, solvent DMSO-d$_6$):2.0 ppm,d,2H; 2.35 ppm,m,1H; 2.4–2.65 ppm,m+m,2H+2H; 3 3 ppm,m,2H: 3.65 ppm,m,2H; 3.80 ppm,-m,2H; 3.95 ppm,m,2H: 7.05–7.25 ppm,dd+td+t 1H+1H+2H; 7.35 ppm, dd,2H; 7.65 ppm,m,1H; 7.9 ppm,dd,1H

Stage G

A mixture of 10 g of the product obtained in the preceding stage, 150 ml of tetrahydrofuran and 150 ml of 2N hydrochloric acid is heated to reflux for 30 minutes. The tetrahydrofuran is then concentrated under vacuum and the product is filtered off to isolate 2,4-dioxo-3-{2-[3-(4-fluorophenacyl)-1-azetidinyl]ethyl},1,2,3,4-tetrahydroquinazoline hydrochloride. The precipitate is rinsed with acetone and dried under vacuum.

Yield: 80%

Melting point: 220° C. (decomposition)

EXAMPLE 33

6-{2-[3-(4 Fluorophenacyl)-1-pyrrolidinyl]ethyl}-7-methyl-5-oxo-5H-thiazolo[3,2-a]pyrimidine dihydrochloride 9.8 g of 3-(4-fluorophenacyl)pyrrolidine, 10.31 g of 6-(2-chloroethyl)-7-methyl-5-oxo-5H-thiazolo[3,2-a]-pyrimidine, 10 g of sodium hydrogen carbonate and 150 ml of toluene are brought to reflux for 50 hours. The mixture is filtered and the toluene is concentrated under vacuum. The oil obtained is then purified by two chromatographic runs on columns of 70–230 mesh silica gel using, first, a mixture of dichloromethane, methanol and ammonia solution (93:7:0.7 V/V/V), and then a mixture of ether, hexane and methanol (60:30:10 V/V/V), as eluant.

The corresponding dihydrochloride is obtained in ethanol.

Yield: 24%

Melting point: 162°–164° C.

EXAMPLE 34

(−)-2,4-Dioxo-3-{2-[3-(4-fluorophenacyl)-1-pyrrolidinyl]ethyl}-1,2,3,4-tetrahydroquinazoline hydrochloride A mixture of 25.04 g of 3-(4-fluorophenacyl)pyrrolidine and 42 g of (−)-di-para-toluoyltartaric acid in 600 ml of ethanol is heated to 55° C. for 3 minutes. Evaporation of the solvent yields a compound which, after 3 recrystallizations in a mixture of acetone and methanol, leads to 15 g of a white solid.

The amine is liberated with potassium hydroxide solution.

The final product is then prepared according to the process described in Example 10.

Yield: 16%

Melting point: 170°–171° C.

Enantiomeric purity: >99% (measured by HPLC)

Optical rotation C=1% in CHCl$_3$: $[\alpha]_d^{22} = -22.1$

EXAMPLE 35

(+)-2,4-Dioxo-3-(2-[3-(4-fluorophenacyl)-1-pyrrolidinyl]ethyl}-1,2,3,4-tetrahydroquinazoline hydrochloride The filtrates of the three recrystallizations of Example 34 are combined and the solvent is then evaporated off. The amine is liberated with potassium hydroxide solution. The base thereby obtained is salified with (+)-di-para-toluoyltartaric acid in ethanol at 55° C. (+)-2,4-Dioxo-3-{2-[3-(4-fluorophenacyl)-1-pyrrolidinyl]ethyl}-1,2,3,4-tetrahydroquinazoline hydrochloride is then prepared according to the process described in Example 34.

Yield: 16%

Melting point: 151° C.

Enantiomeric purity: >99% (measured by HPLC)

Optical rotation C =1% in CHCl$_3$: $[\alpha]_D^{22} = +22.3$

TABLE I

Compounds of general formula I

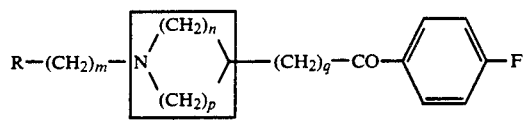

A

| EXAMPLE No. | R | m | A | q | NMR Spectrum (Solvent) |
|---|---|---|---|---|---|
| 1 | ![structure: cyanoimidazole with N-C(CH3)=C(OH)-CH3 substituent] | 2 | —N⟨piperidine⟩ | 0 | $^1$H NMR (DMSO-$d_6$) Salt 2.0–2.2 ppm, m, 4H; 2.35 ppm, s, 3H; 2.7–4.0 ppm, m, 9H; 7.4–7.7 ppm, m, 2H; 8.1 ppm, s, 1H; 8–8.4 ppm, m, 2H |
| 2 | ![2-fluorobenzyl-piperazine-2,6-dione] | 3 | —N⟨piperidine⟩ | 0 | $^1$H NMR (DMSO-$d_6$) Salt 1.8–2.3 ppm, m, 6H; 2.8–3.6 ppm, m, 9H; 3.6 ppm, s, 4H; 3.8 ppm, s, 2H; 7.2–7.6 ppm, m, 6H; 8.0–8.3 ppm, m, 2H; 10.0–11.0 ppm, 1H exchangeable |
| 3 | ![2-pyridylmethyl-piperazine-2,6-dione] | 3 | —N⟨piperidine⟩ | 0 | $^1$H NMR (CDCl$_3$) Salt 1.8–2.8 ppm, m, 6H; 2.8–4.1 ppm, m, 15H; 7.0–7.6 ppm, m, 4H; 7.6–8.3 ppm, m, 3H; 8.6 ppm, m, 1H |
| 4 | ![2-fluorobenzyl-piperazine-2,6-dione] | 4 | —N⟨piperidine⟩ | 0 | $^1$H NMR (DMSO-$d_6$) Salt 1.3–2.2 ppm, m, 8H; 2.6–4.0 ppm, s+m+s+m, 2H+2H+4H+7H; 7.1–7.7 ppm, m, 6H; 8.0–8.3 ppm, m, 2H |
| 5 | ![2-fluorobenzyl-piperazine-2,6-dione] | 3 | —N⟨pyrrolidine-methyl⟩ | 1 | $^1$H NMR (CDCl$_3$ + DMSO-$d_6$) Salt 1.2–2.2 ppm, m, 4H; 2.5–4.0 ppm, m+m+s+m+m, 2H+2H+4H+8H+1H; 4.3 ppm, m, 2H; 4.8–5.5 ppm, 1H exchangeable; 6.9–7.6 ppm, m, 6H; 7.8–8.2 ppm, m, 2H 8.0–10 ppm, 1H exchangeable |
| 6 | ![2-fluorobenzyl-piperazine-2,6-dione] | 3 | —N⟨piperidine-methyl⟩ | 1 | $^1$H NMR (CDCl$_3$) Salt 1.4–3.3 ppm, m+m, 6H+9H; 3.4–3.9 ppm, s+m+s, 4H+2H+2H; 4.25 ppm, s, 4H; 6.0–8.0 ppm, 1H exchangeable; 7.1–7.8 ppm m, 6H; 7.9–8.3 ppm, m, 2H |
| 7 | ![2-pyrimidinyl-piperazine] | 3 | —N⟨piperidine⟩ | 0 | $^1$H NMR (DMSO-$d_6$) Salt 1.6–2.5 ppm, m, 6H; 2.7–4.5 ppm, m+m+m, 4H+12H+1H; 4.5–5.1 ppm, 1H exchangeable; 6.85 ppm, t, 1H; 7.4 ppm, t, 2H; 8–8.3 ppm, dd, 2H; 8.5 ppm, d, 2H; 10.8–12.2 ppm, 1H exchangeable |

TABLE I-continued

Compounds of general formula I

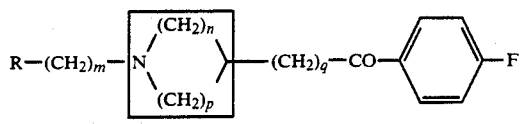

A

| EXAMPLE No. | R | m | A | q | NMR Spectrum (Solvent) |
|---|---|---|---|---|---|
| 8 | $H_2NCO$-imidazo[pyrimidine with CH_3, OH] | 2 | —N⟨piperidine⟩— (4-) | 0 | $^1H$ NMR (DMSO-$d_6$) Salt 1.9 ppm, m, 2H; 2.04 ppm, m, 2H; 2.54 ppm, s, 3H; 2.93 ppm, m, 2H; 3.13 ppm, m, 5H; 3.7 ppm, m, 2H; 7.23 1H exchangeable; 7.4 ppm, t, 2H; 7.43 ppm, 1H exchangeable; 8.1 ppm, dd, 2H; 8.14 ppm, s, 1H; 9.93 ppm 1H exchangeable; 11.6 ppm, m, 1H |
| 9 | $H_2NCO$-imidazo[pyrimidine with CH_3, OH] | 2 | —N⟨piperidine⟩ (3-) | 1 | $^1H$ NMR (DMSO-$d_6$)Base 1.72 ppm, m, 1H; 2.2 ppm, m, 1H; 2.53 ppm, s, 3H; 2.75 ppm, m, 1H; 2.90 ppm, t, 2H; 3.07 ppm, m, 1H; 3.20 ppm, m, 1H; 3.35 ppm, d, 5H; 3.62 ppm, m, 1H; 3.84 ppm, m, 1H; 7.23 ppm, s, 1H; 7.35 ppm, dd, 2H; 7.41 ppm, s, 1H; 8.05 ppm, dd, 2H; 8.10 ppm, s, 1H; 11.54 ppm, s, 1H |
| 10 | 3-methyl-quinazoline-2,4-dione-1-yl | 2 | —N⟨piperidine⟩ (3-) | 1 | $^1H$ NMR (DMSO-$d_6$) Salt 1.5–2.6 ppm, m, 2H; 1.5–2.6 ppm, m, 1H; 2.5–3.0 ppm, m, 2H; 3.0–3.7 ppm, m, 6H; 4.2 ppm, t, 2H; 7.0–8.3 ppm, m, 8H |
| 11 | $[F-C_6H_4]_2$CH—O | 2 | —N⟨piperidine⟩ (4-) | 0 | $^1H$ NMR (CDCl$_3$) Base 1.9 ppm, m, 4H; 2.8 ppm, m, 4H; 2.7 ppm, t, 2H; 3.2 ppm, m, 1H; 3.6 ppm, t, 2H; 5.4 ppm, s, 1H; 7.2 ppm, m, 10H; 8.0 ppm, m, 2H |
| 12 | benzodioxane-CH$_2$NH— | 3 | —N⟨piperidine⟩ (4-) | 0 | $^1H$ NMR (CDCl$_3$)Base 1.0–3.7 ppm, m+m+m, 6H+1H+10H; 2.4–3.1 ppm, 1H exchangeable; 4.0–4.5 ppm, m, 3H; 6.9 ppm, m, 4H; 7.0–7.4 ppm, m, 2H; 7.2–8.9 ppm, m, 2H |
| 13 | $H_2NCO$-imidazo[pyrimidine with CH_3, OH] | 2 | —N⟨piperidine⟩ (3-) | 1 | $^{13}C$ NMR (DMSO-$d_6$) Base 17.4 ppm; 19.5 ppm; 30.0 ppm; 54.6 ppm; 55.6 ppm; 100.2 ppm; 115.2 ppm; 115.3 ppm; 123.3 ppm; 130.8 ppm; 132.6 ppm; 133.4 ppm; 151.3 ppm; 155.6 ppm; 165.0 ppm; 166.3 ppm; 196.6 ppm; |
| 14 | 2-methylbenzyl-piperazine-2,6-dione | 3 | —N⟨piperidine⟩ (4-) | 0 | $^1H$ NMR (DMSO-$d_6$) Salt 1.5–2.5 ppm, s+m, 3H+7H; 2.8–4.0 ppm, m+s+s+m, 2H+2H+4H+6H; 7.0–7.6 ppm, m, 6H; 8.0–8.4 ppm, m, 2H; 10–11.5 ppm, 1H exchangeable |
| 15 | 3-methylbenzyl-piperazine-2,6-dione | 3 | —N⟨piperidine⟩ (4-) | 0 | $^1H$ NMR (DMSO-$d_6$) Salt 1.6–2.4 ppm, m, 7H; 2.3 ppm, s, 3H; 2.4–3.9 ppm, m+s+s+m, 2H+2H+4H+6H; 7.0–7.7 ppm, m, 6H; 8.0–8.4 ppm, m, 2H; 9.5–11.0 ppm, 1H exchangeable |

TABLE I-continued

Compounds of general formula I

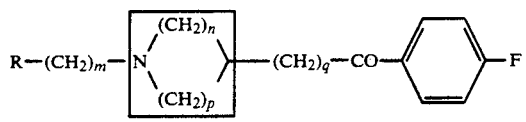

A

| EXAMPLE No. | R | m | A | q | NMR Spectrum (Solvent) |
|---|---|---|---|---|---|
| 16 | 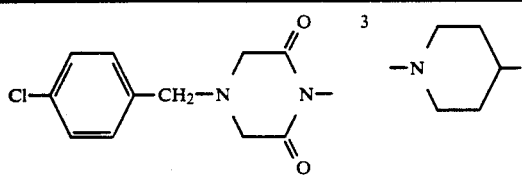 | 3 | 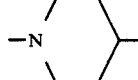 | 0 | ¹H NMR (CDCl₃) Salt 1.6–2.5 ppm,m,7H; 2.7–4.0 ppm,m+s+ s+m,2H+2H+4H+6H; 7.0–7.6 ppm,m,6H; 7.8–8.3 ppm,m,2H; 1 0.0–11.0 ppm,m,1H exchangeable |
| 17 | 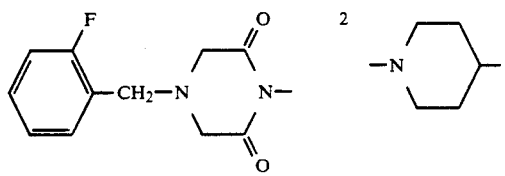 | 2 |  | 0 | ¹H NMR (CDCl₃) Salt 1.8–2.2 ppm, m, 4H; 2.8–4.0 ppm, m, 9H; 3.3 ppm, m, 4H; 3.6 ppm, s, 2H; 7.7–7.1 ppm, m, 6H, 8.0–8.3 ppm, m, 2H; 10.0– 11.0 ppm, 1H exchangeable |
| 18 | 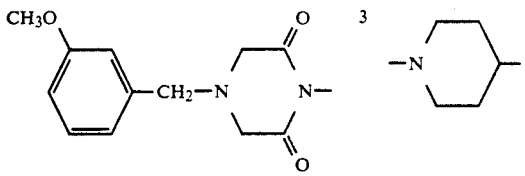 | 3 |  | 0 | ¹H NMR (DMSO-d₆) Salt 1.8–2.8 ppm, m, 7H; 2.8–3.6 ppm, m, 6H; 3.5 ppm, s, 4H; 3.7 ppm, s, 2H; 3.8–4.0 ppm, m, 2H; 3.9 ppm, s, 3H; 6.8–7.5 ppm, m, 6H; 8.0–8.3 ppm, m, 2H |
| 19 | 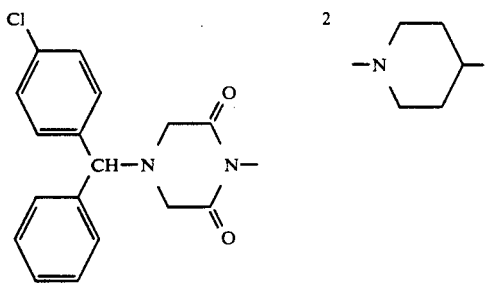 | 2 | 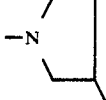 | 0 | ¹H NMR (DMSO-d₆) Salt 1.7–2.3 ppm, m, 4H; 2.7–4.0 ppm, m, 7H; 3.5 ppm, s, 4H; 3.9–4.2 ppm, m, 2H; 4.8 ppm, s, 1H; 7.2–7.6 ppm, m, 11H; 8.0–8.4 ppm, m, 2H; 10.5–11.5 ppm, 1H exchangeable |
| 20 | 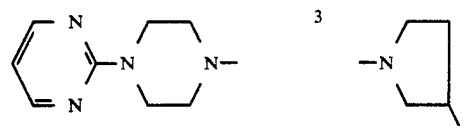 | 3 | 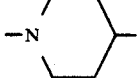 | 1 | ¹H NMR (DMSO-d₆) Salt 1.5–4.2 ppm, m+m+m,4H+14H+5H; 4.5–5.0 ppm, 1H exchangeable; 6.7–6.9 ppm, t, 1H; 7.2–7.5 ppm, t, 2H; 7.9–8.2 ppm, dd, 2H; 8.4–8.5 ppm, d, 2H; 11.0–12.0 ppm 1H exchangeable |
| 21 | 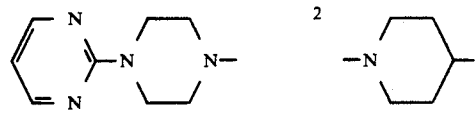 | 2 | 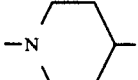 | 0 | ¹H NMR (D₂O) Salt 1.8–2.5 ppm, m, 4H; 3.2–4.3 ppm, m, 17H; 6.9 ppm, t, 1H; 7.1–7.6 ppm, m, 2H; 7.8–8.3 ppm, m, 2H; 8.5 ppm, d, 2H |
| 22 | 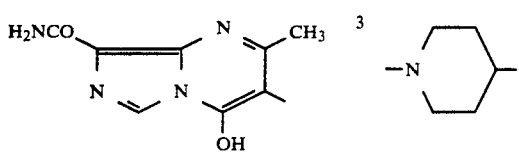 | 3 | | 0 | ¹³C NMR (DMSO-d₆) Salt 21.6 ppm; 22.7 ppm; 25.6 ppm; 50.9 ppm; 55.5 ppm; 103.5 ppm; 114.9 ppm; 115.7 ppm; 123.3 ppm; 131.1 ppm; 132.0 ppm; 132.8 ppm; 150.2 ppm; 156.1 ppm; 164.4 ppm; 165.0 ppm; 199.5 ppm |

TABLE I-continued

Compounds of general formula I

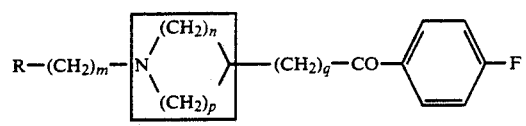

A

| EXAMPLE No. | R | m | A | q | NMR Spectrum (Solvent) |
|---|---|---|---|---|---|
| 23 | 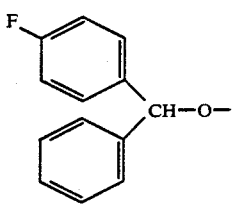 | 2 | 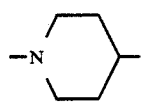 | 0 | $^1$H NMR (DMSO-d$_6$) Salt 1.7–2.3 ppm, m,4H; 2.7–4.0 ppm, m+m+m+m, 2H+4H+2H+1H; 5.7 ppm, s, 1H; 6.1 ppm, s, 2H; 6.9–7.6 ppm, m, 11H; 7.85–8.25 ppm, m, 2H |
| 24 | 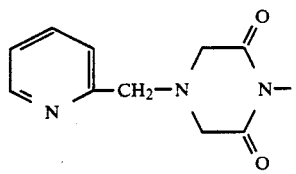 | 2 | 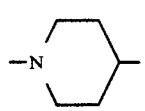 | 0 | $^1$H NMR (DMSO-d$_6$)Salt 1.8–2.3 ppm, m, 4H; 3.0–3.7 ppm, m, 7H; 3.9 ppm, s, 4H; 4.0–4.2 ppm, m, 2H; 4.4 ppm, s, 2H; 7.2–7.6 ppm, t, 2H; 7.8–8.6 ppm, m, 5H; 8.6–9.0 ppm, m, 1H |
| 25 | 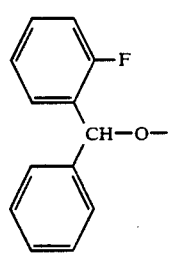 | 2 | 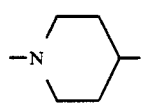 | 0 | $^1$H NMR (CDCl$_3$) Salt 2.0–2.5 ppm,m,4H; 3.0–4.0 ppm,m,9H; 5.25 ppm,s,1H; 6.3 ppm,s,2H; 7.1–7.6 ppm,m,10H; 7.9–8.2 ppm,dd,2H; 12–13 ppm, 1H exchangeable |
| 26 | 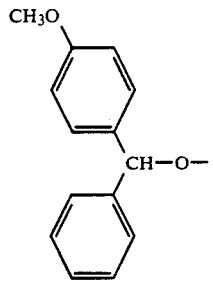 | 2 | 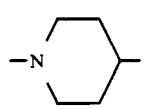 | 0 | $^1$H NMR (DMSO-d$_6$) Salt 1.5–2.3 ppm,m,4H; 2.7–4.0 ppm,m,9H; 3.75 ppm,s,3H; 5.5 ppm,s,1H; 6.1 ppm,s,2H; 6.8–7.6 ppm,m,11H; 8.0–8.3 ppm,m,2H |
| 27 | 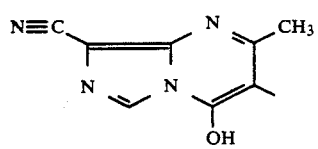 | 2 | 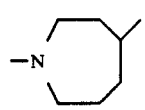 | 0 | $^{13}$C NMR (DMSO) Salt 17.2 ppm; 19.9 ppm; 22.2 ppm; 25.3 ppm; 29.0 ppm; 43.3 ppm; 51.7 ppm; 53.8 ppm; 54.6 ppm; 92.1 ppm; 101.2 ppm; 114.4 ppm; 115.4 ppm; 115.7 ppm; 126.0 ppm; 131.0 ppm; 131.2 ppm; 132.4 ppm; 137.6 ppm; 151.1 ppm; 155.5 ppm; 163.3 ppm; 166.7 ppm; 200.7 ppm |
| 28 | 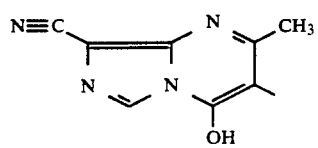 | 2 | 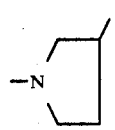 | 1 | $^{13}$C NMR (DMSO-d$_6$) Salt 21.0 ppm; 29.0 ppm; 31.8 ppm; 41.7 ppm; 52.1 ppm; 53.0 ppm; 57.5 ppm; 91.6 ppm; 101 ppm; 114.7 ppm; 115.7 ppm; 126.5 ppm; 130.8 ppm; 133.0 ppm; 137.6 ppm; 150.9 ppm; 155.5 ppm; 165 ppm; 197.2 ppm |

TABLE I-continued

Compounds of general formula I

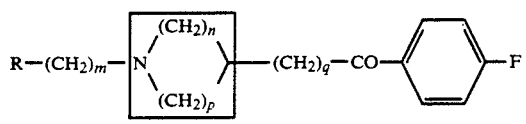

A

| EXAMPLE No. | R | m | A | q | NMR Spectrum (Solvent) |
|---|---|---|---|---|---|
| 29 | 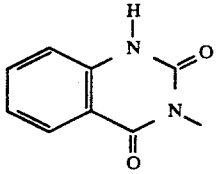 | 2 | 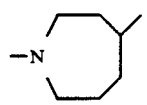 | 0 | $^1$H NMR (DMSO-d$_6$) Salt 1.4–2.2 ppm, m+m+m, 1+1+4H; 3.0–4.1 ppm, m+m+m, 1+1+5H; 4.3 ppm, m, 2H; 7.2 ppm, m, 2H; 7.35 ppm, t, 2H; 7.7 ppm, t, 1H; 7.95 ppm, d, 1H; 8.1 ppm, dd, 2H |
| 30 | 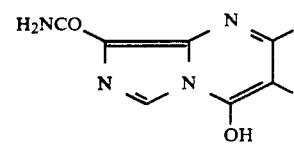 | 2 |  | 0 | $^{13}$C NMR (DMSO-d$_6$) Salt 17.2 ppm; 19.8 ppm; 42.7 ppm; 43.6 ppm; 54.3 ppm; 99.9 ppm; 115.0 ppm; 115.6 ppm; 115.9 ppm; 123.4 ppm; 131.2 ppm; 131.3 ppm; 131.9 ppm; 132.5 ppm; 151.4 ppm; 155.8 ppm; 163.3 ppm; 164.3 ppm; 166.6 ppm; 200.6 ppm; 200.9 ppm |
| 31 | 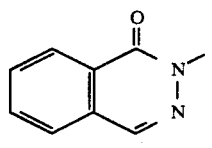 | 2 | 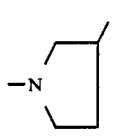 | 1 | $^1$H NMR (DMSO-d$_6$) Salt 1.7–2.2 ppm, m, 2H; 2.8 ppm, m, 1H; 3.0 ppm, m, 2H; 3.2–3.9 ppm, m, 6H; 4.5 ppm, t, 2H; 7.3–8.5 ppm, m, 9H |
| 32 | 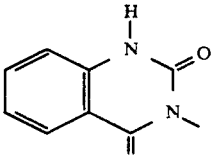 | 2 |  | 1 | $^1$H NMR (DMSO-d$_6$) Salt 3–3.3 ppm, m, 1H; 3.4–3.7 ppm, m+d, 2H+2H; 4.1 ppm, m, 2H; 3.9 ppm, m, 2H; 4.25 ppm, m, 2H; 7.15–7.30 ppm, d+t, 1H+1H; 7.4 ppm, t, 2H; 7.7 ppm, t, 1H; 7.95 ppm, d, 1H; 8.05 ppm, dd, 2H |
| 33 | 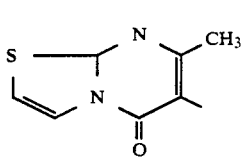 | 2 | 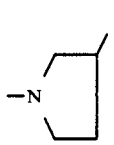 | 1 | $^1$H NMR (DMSO-d$_6$) Salt 1.6–2.0 ppm, m, 1H; 2.1–2.4 ppm, m, 1H; 2.45 ppm, s, 3H; 2.5–4.2 ppm, m, 11H; 7.26–7.6 ppm, d+m, 1H+2H; 7.95–8.15 ppm, m, 3H; 11–11.5 ppm, m, 2H exchangeable |

Pharmacological Study

EXAMPLE 36

Histamine Antaqonism

Male albino guinea pigs (350–400 g) are subjected to a water diet for 18 hours before the test and anesthetized intraperitoneally with ethyl carbamate at a dose of 1.25 g/kg. A catheter is introduced into a carotid artery to measure the arterial blood pressure by means of a P23ID pressure cell connected to a Gould 2400® recorder Another catheter is introduced into a jugular vein and is used for injecting the test compounds. The trachea is cannulated and the guinea pig is subjected to assisted respiration using a Havard respirator for small animals.

The guinea pig's temperature is maintained in the vicinity of 37° C. using a heating lamp. A needle inserted into the tracheal cannula is connected to a P50 pressure cell enabling the tracheal pressure to be recorded.

The guinea pigs are pretreated with d-tubocurarine (1 mg/kg i.v.). Histamine is then injected intravenously at a dose of 10 μg/kg. This dose induces broncho-constriction and leads to an increase in the tracheal pressure. The histamine injections are repeated several times at 10-minute intervals until the response has stabilized. The compounds of the invention are then injected i.v. at cumulative doses, and the dose inhibiting by 100% the increase in tracheal pressure caused by the injection of histamine (ID$_{100}$) is determined. The ID$_{100}$ of the compounds of the invention is between 10 and 250 μg/kg.

EXAMPLE 37

5-HT$_2$ Antagonism

Male Sprague-Dawley rats (350–400 g) are anesthetized i.p. with pentobarbital (45 mg/kg). The trachea is cannulated and the animals are subjected to artificial respiration. The vagus nerves are sectioned. A catheter is placed in a carotid artery to record the arterial blood pressure. A second catheter is placed in the vein of the penis and is used for the injections. The animals' temperature is taken and is maintained at 37° C. The rats are pretreated with d-tubocurarine (1 mg/kg i.v.) an prazosin (1 mg/kg i.v.). 5-Hydroxytryptamine is injected i.v. at a dose of 100 µg/kg twice, separated by an interval of 10 minutes, so as to determine the rise in the systolic arterial blood pressure of each rat 10 minutes later, the compounds of the invention are injected at the lowest dose and injection of 5-hydroxytryptamine is performed again 10 minutes later. 3 or 4 cumulative doses of the compounds of the invention are tested in the same manner. The percentages of the hypertensive response which are obtained at the different doses are calculated in order to determine the $ID_{50}$, the dose inhibiting the hypertensive response by 50%. The results of this study are presented in Table II.

TABLE II

| COMPOUND | $ID_{50}$ (µg/kg i.v.) |
|---|---|
| EXAMPLE 1 | 4.5 |
| EXAMPLE 2 | 14.0 |
| EXAMPLE 6 | 3.7 |
| EXAMPLE 8 | 18.0 |
| EXAMPLE 9 | 10.0 |
| EXAMPLE 10 | 5.4 |

EXAMPLE 38

$\alpha_1$ Antagonism

Male Sprague-Dawley rats (300–400 g) which have been subjected to a water diet are anesthetized with ethyl ether. A cannula is placed in the trachea. The spinal cord is destroyed by means of a steel rod and artificial respiration is instituted at once. The vagus nerves are sectioned. The carotid arteries are ligated and a catheter is placed in one of them to record the arterial blood pressure. A second catheter is placed in the vein of the penis and is used for the injections. The animals' temperature is taken and is maintained at 36° C. The rats are pretreated with a $\beta$-blocker (Tertatolol 00 µg/kg i.v.). Phenylephrine is injected at a dose of 4 µg/kg i.v. Two identical injections are performed, separated by an interval of 10 minutes. The compounds of the invention and ketanserin are injected at the lowest dose and injection of phenylephrine is performed again 10 minutes later. 3 or 4 cumulative doses of the compounds of the invention and of ketanserin are tested in the same manner. The values for the percentage inhibition of the hypertensive response which are obtained at the different doses are calculated in order to determine the $ID_{50}$.

The results of this study are given in Table III. As the results in the table demonstrate, the compounds of the invention are much more potent $\alpha_1$ antagonists than ketanserin.

TABLE III

| COMPOUND | $ID_{50}$ (µg/i.v.) |
|---|---|
| EXAMPLE 2 | 376 |
| EXAMPLE 4 | 369 |
| EXAMPLE 5 | 494 |
| EXAMPLE 8 | 240 |
| EXAMPLE 9 | 26 |
| EXAMPLE 10 | 18 |
| EXAMPLE 13 | 147 |
| KETANSERIN | 3,600 |

EXAMPLE 39

5-HTP Antagonism

4 Female Wistar rats (270±30 g), fasted for approximately 24 hours, are used. At the beginning of the test, they are administered the "control" solution or solutions of 5-hydroxytryptophan at a dose of 320 mg/kg. The animals are then placed under observation in transparent cages. Three parameters are assessed in the study: "forepaw treading", "flat body posture" and "head twitches". "Forepaw treading" corresponds to a pedalling motion of the forelimbs. This parameter is measured 80 minutes after the administration of 1,5-hydroxytryptophan and during a ten-minute observation period. This time is divided into 5- second periods and, if a movement is observed in this period, a score of 1 is assigned, the maximum score being 30 for the ten minutes of observation and for each animal. The parameter "head twitches" relates to the number of twitches of the head of the animals observed during 10 minutes. This parameter is assessed 90 minutes after the administration of 1,5-hydroxytryptophan and during a 10- minute period. "Flat body posture" corresponds to a flattening of the body which lasts for more than 10 minutes. This parameter is assessed throughout the period of observation of the animals.

The results of these studies, which are presented in Tables IV and V, demonstrate that the compounds of the invention are potent 5-HTP antagonists. The results presented in Table VI also demonstrate that the compounds of the invention are well absorbed orally, which constitutes a very considerable advantage in therapy.

TABLE IV

| | 5-HTP antagonism: Compounds tested subcutaneously | | |
|---|---|---|---|
| | $ED_{50}$ (mg/kg) | | |
| COMPOUND | FPT* | FBP** | HT*** |
| EXAMPLE 1 | 40 | 0.04 | >40 |
| EXAMPLE 2 | 10 | 0.31 | 5 |
| EXAMPLE 3 | 1.25 | 0.31 | 5 |
| EXAMPLE 4 | 5 | 10 | 10 |
| EXAMPLE 5 | 10 | 0.31 | >10 |
| EXAMPLE 6 | 2.5 | 1.25 | 1.25 |
| EXAMPLE 7 | 1.25 | 1.25 | >10 |
| EXAMPLE 10 | 0.31 | 0.16 | 2.5 |
| EXAMPLE 15 | 10 | 2.5 | 5 |
| EXAMPLE 18 | 5 | 2.5 | 5 |
| EXAMPLE 21 | 2.5 | 0.63 | 1.25 |

TABLE V

| | $ED_{50}$ (mg/kg) | | |
|---|---|---|---|
| COMPOUND | FPT* | FBP** | HT*** |
| EXAMPLE 8 | 10 | 0.63 | >10 |

FPT* = forepaw treading
FBP** = flat body posture
HT*** = head twitches

EXAMPLE 40

Tablets containing 10 mg
2,4-dioxo-3-{2-[3-(4-fluorophenyl)-1-pyrrolidinyl]ethyl}-1,2,3,4-tetrahydroquinazoline (DFPPETQ)

DFPPETQ—10 g
Wheat starch—100 g
Corn starch—20 g
Magnesium stearate—15 g
Talc—20 g
per 1000 tablets containing 10 mg of active principle.

We claim:
1. A compound of general formula I:

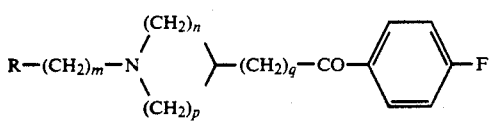

in which:
m is an integer from 2 to 4,
n and p, which may be identical or different, each are an integer from 1 to 3, their total not exceeding 3,
q is 0 or 1, and
R is:
a group of formula (A):

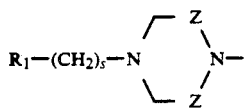

in which s is an integer from 0 to 4, Z is a methylene radical or a carbonyl radical and $R_1$ is either a phenyl radical (optionally substituted with one or more halogen atoms or with a linear or branched lower alkyl radical containing from 1 to 5 carbon atoms or a lower alkoxy radical containing from 1 to 5 carbon atoms), or a diphenylmethylene radical (optionally substituted with one or more halogen atoms or with a lower alkyl radical or lower alkoxy radical), or an unsaturated five- or six-membered ring containing one or two nitrogen atoms,
or a radical of the formula (B):

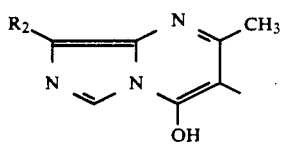

in which $R_2$ is a carbamoyl radical, a cyano radical, a carboxy radical or an alkoxycarbonyl radical containing from 2 to 7 carbon atoms,
or a 2,4-dioxo-1,2,3,4-tetrahydroquinazolinyl radical on condition, however, that, in this case, q equals 1, and n and p do not simultaneously represent the number 2,
or a 1-oxophthalazinyl radical,
or a 5-oxothiazolo[3,2-a]pyrimidinyl radical (optionally substituted with one or more halogen atoms or with a linear or branched alkyl radical containing from 1 to 5 carbon atoms or a lower alkoxy radical containing from 1 to 5 carbon atoms),
or a benzhydryloxy group (in which the phenyl radicals are optionally substituted with one or more halogen atoms or with a linear or branched alkyl radical containing from 1 to 5 carbon atoms or an alkoxy radical containing from 1 to 5 carbon atoms),
or a group of formula C:

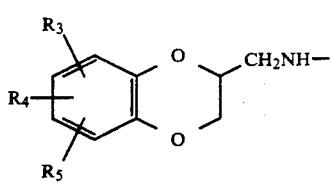

in which $R_3$, $R_4$ and $R_5$, which may be identical or different, each are a halogen atom, an alkoxy radical having 1 to 5 carbon atoms or a linear or branched alkyl radical having 1 to 5 carbon atoms, their possible stereoisomers and their addition salts with a pharmaceutically acceptable inorganic or organic acid.

2. A compound of claim 1 being 8-cyano-3-{b 2-(4-(4-fluorobenzoyl)piperidino]-ethyl}-4-hydroxy-2-methylimidazo[1,5-a]pyrimidine, or an addition salt thereof with a pharmaceutically acceptable inorganic or organic acid.

3. A compound of claim 1 being 2,4-dioxo-3-{2-[3-(4-fluorophenacyl)-1-pyrrolidinyl)ethyl}-1,2,3,4-tetrahydroquinazoline, or an addition salt thereof with a pharmaceutically acceptable inorganic or organic acid.

4. A compound of claim 1 being 8-carbamoyl-3-{2 [3-(4-fluorophenacyl)-1-pyrrolidinyl]ethyl}-4-hydroxy-2-methylimidazol[1,5-a]pyrimidine, or an addition salt thereof with a pharmaceutically acceptable inorganic or organic acid.

5. A compound of claim 1 being 1-{3-[4-(4fluorobenzoyl)piperidino]propyl}-4-(2-fluorobenzyl) piperazine 2,6-dione, or an addition salt thereof with a pharmaceutically acceptable inorganic or organic acid.

6. A compound of claim 1 being 1-{3-[4-(4-fluorobenzoyl) piperidino]propyl}-4-(2-hyrimidinyl) piperazine, or an addition salt thereof with a pharmaceutically acceptable inorganic or organic acid.

7. A pharmaceutical composition containing, as active principle, a compound as claimed in inclusive claim 1, in combination or mixed with a pharmaceutically acceptable, non-toxic inert vehicle or excipient.

8. The pharmaceutical composition as claimed in claim 7 containing the active principle in an amount of 0.5 to 100 mg.

9. A method for the treatment of diseases requiring $\alpha_1$-adrenergic antagonists, serotonin antagonists and histamine antagonists comprising the step of administering to the living being an effective amount of a compound of claim 1.

10. The method of claim 9 wherein a pharmaceutical composition is administered, wherein the active compound is present in an amount of 0.5 to 100 mg.

11. A method of claim 9 wherein the compound is administered in the form of a pharmaceutical composition thereof in which it is combined with a pharmaceutically acceptable vehicle or excipient.

* * * * *

UNITED STATES PATENT AND TRADEMARK OFFICE
CERTIFICATE OF CORRECTION

PATENT NO. : 5,077,288

DATED : Dec. 31, 1991

INVENTOR(S) : Gilbert Lavielle, Francis Colpaert, Michel Laubie

It is certified that error appears in the above-identified patent and that said Letters Patent is hereby corrected as shown below:

```
Column 4, line 59; "2 (4-fluorophenyl)" should read
--2-(4-fluorophenyl) --
Column 6, approximately line 38; "[5-a]" should read -- [1,5-a] --.
Column 6, line 68; "pp,s," should read -- ppm,s,--.
Column 7, approximately line 35; "silica using" should read
   -- silica, using --.
Column 8, line 26; "hours," should read -- hours'  --.
Column 8, line 67; delete "25".
Column 10, approximately line 27; "methylimidazol" should read
   -- methylimidazo --.
Column 10, approximately line 34; "methanol After" should read
   -- methanol. After --.
Column 10, line 34; "hours," should read -- hours' --
Column 11, line 59; "is take" should read -- is taken --.
Column 12, line 1; "2H  3.65" should read -- 2H; 3.65 --.
Column 15, line 53; "piperzine" should read -- piperazine --.
Column 16, approximately line 28; "4,4," should read--4,4' --.
Column 16, approximately line 50; "ethanol After" should read
   -- ethanol. After --.
Column 16, approximately line 52; "removed The" should read
   -- removed. The --.
Column 17, approximately line 44; "CDCl$_3$):1:  1.65" should read
   -- CDCl$_3$):    1.65 --.
Column 17, approximately line 45/46; "7.1 ppm,dd,2H;" should read
   -- 7.1 ppm,t,2H; --.
Column 17, line 46; "7.95 ppm,5,2H" should read --7.95 ppm, dd, 2H--.
Column 17, approximately line 50; "ethoxycarbonylperhyiroazepine"
   should read -- ethoxycarbonylperhydroazepine --.
Column 20, line 9; "ppm,q,2H:" should read --ppm, q, 2H; --.
Column 20, line 51; "2H;  4.1" should read -- 2H; 4 ppm, m, 2H;4.1--.
Column 20, line 52; delete "4.1 ppm,d,2H;".
Column 21, approximately line 49; "3  3" should read -- 3.3 --.
```

Page 1 of 2

UNITED STATES PATENT AND TRADEMARK OFFICE
CERTIFICATE OF CORRECTION

PATENT NO. : 5,077,288
DATED : Dec. 31, 1991
INVENTOR(S) : Gilbert Lavielle, Francis Colpaert, Michel Laubie It is certified that error appears in the above-identified patent and that said Letters Patent is hereby corrected as shown below:

Column 22, line 50; "-3-(2-" should read -- -3-{2- --.
Column 31, line 61; "corder Another" should read --corder. Another--.
Column 33, line 5; "an" should read -- and --.
Column 33, line 9; "rat 10" should read -- rat. 10 --.
Column 33, line 42; "(Tertatolol 00" should read
 -- (Tertatolol 100 --.
Column 35, line 14; "3, their total not exceeding 3," should read
 --3, their total not exceeding 5,--.
Column 36, line 20; "-3-{b 2-" should read -- -3- {2- --.
Column 36, line 31; "methylimidazol" should read --methylimidazo--.
Column 36, line 34; "(4fluoroben-" should read --(4-fluoroben- --.
Column 36, line 39; "-hyrimidinyl" should read --pyrimidinyl--.

Signed and Sealed this

Fifteenth Day of June, 1993

Attest:

MICHAEL K. KIRK

Attesting Officer

Acting Commissioner of Patents and Trademarks